US012582306B2

(12) United States Patent
Lee et al.

(10) Patent No.: US 12,582,306 B2
(45) Date of Patent: Mar. 24, 2026

(54) SCANNER FOR DENTAL TREATMENT, AND DATA TRANSMISSION METHOD OF SAME

(71) Applicant: MEDIT CORP., Seoul (KR)

(72) Inventors: Seung Jin Lee, Seoul (KR); Hyeong Seok Kim, Seoul (KR)

(73) Assignee: MEDIT CORP., Seoul (KR)

( * ) Notice: Subject to any disclaimer, the term of this patent is extended or adjusted under 35 U.S.C. 154(b) by 311 days.

(21) Appl. No.: 18/265,151

(22) PCT Filed: Dec. 2, 2021

(86) PCT No.: PCT/KR2021/018163
§ 371 (c)(1),
(2) Date: Jun. 2, 2023

(87) PCT Pub. No.: WO2022/119363
PCT Pub. Date: Jun. 9, 2022

(65) Prior Publication Data
US 2024/0000306 A1 Jan. 4, 2024

(30) Foreign Application Priority Data
Dec. 4, 2020 (KR) ........................ 10-2020-0168733

(51) Int. Cl.
*A61B 1/24* (2006.01)
*A61B 1/00* (2006.01)
(Continued)

(52) U.S. Cl.
CPC ............ *A61B 1/24* (2013.01); *A61B 1/00006* (2013.01); *A61B 1/00009* (2013.01);
(Continued)

(58) Field of Classification Search
CPC ............ A61B 1/00006; A61B 1/00009; A61B 1/00016; A61B 1/0004; A61B 1/00105;
(Continued)

(56) References Cited

U.S. PATENT DOCUMENTS 7,139,016 B2 * 11/2006 Squilla ............... A61B 1/00048
348/66
8,712,228 B2 4/2014 Inglese et al.
(Continued)

FOREIGN PATENT DOCUMENTS

CN 106413517 A 2/2017
JP 2007-027874 A 2/2007
(Continued)

OTHER PUBLICATIONS

Extended European Search Report dated Sep. 19, 2024 in Application No. 21901051.9.
(Continued)

*Primary Examiner* — Peter D Le
(74) *Attorney, Agent, or Firm* — Sughrue Mion, PLLC

(57) ABSTRACT

An intraoral scanner according to an embodiment of the present disclosure includes: a camera module comprising at least one camera; a communication unit including a first communication module configured to perform wireless communication in a first frequency band, and a second communication module configured to perform wireless communication in a second frequency band; and a processor configured to execute at least one instruction. In addition, the processor is further configured to obtain image data corresponding to at least one image obtained by the at least one camera, perform control such that the image data is transmitted to an external electronic device through the first communication module performing wireless communication in the first frequency band, and perform control such that control signals related to at least one of operations of obtaining transmitting the at least one image are transmitted to and received from the external electronic device through the second communication module performing wireless communication in the second frequency band.

14 Claims, 19 Drawing Sheets

(51) Int. Cl.

| | |
|---|---|
| *A61B 1/045* | (2006.01) |
| *A61B 1/06* | (2006.01) |
| *A61C 9/00* | (2006.01) |
| *G16H 30/40* | (2018.01) |
| *G16H 40/67* | (2018.01) |

(52) U.S. Cl.

CPC ........ *A61B 1/00016* (2013.01); *A61B 1/0004* (2022.02); *A61B 1/00105* (2013.01); *A61B 1/045* (2013.01); *A61B 1/0655* (2022.02); *A61C 9/0053* (2013.01); *A61C 9/0093* (2013.01); *G16H 30/40* (2018.01); *G16H 40/67* (2018.01)

(58) Field of Classification Search

CPC ......... A61B 1/045; A61B 1/0655; A61B 1/24; A61B 5/0013; A61B 5/0022; A61B 5/0088; A61C 9/0053; A61C 9/0093; G16H 30/40; G16H 40/63; G16H 40/67; G16H 50/20; G16H 50/50; H04W 4/80; H04W 88/06

See application file for complete search history.

(56) References Cited

U.S. PATENT DOCUMENTS

| | | | | |
|---|---|---|---|---|
| 10,524,635 | B2 | 1/2020 | Endo | |
| 2004/0152037 | A1* | 8/2004 | Schick | A61B 1/24 |
| | | | | 433/29 |
| 2005/0192478 | A1* | 9/2005 | Williams | A61B 1/0684 |
| | | | | 600/117 |
| 2008/0045789 | A1* | 2/2008 | Sawachi | G02B 7/28 |
| | | | | 600/137 |
| 2010/0179384 | A1* | 7/2010 | Hoeg | A61B 1/042 |
| | | | | 600/109 |

| | | | | |
|---|---|---|---|---|
| 2014/0309491 | A1* | 10/2014 | Karasawa | A61B 1/00016 |
| | | | | 600/103 |
| 2016/0066770 | A1* | 3/2016 | Barbato | A61B 1/00144 |
| | | | | 600/138 |
| 2016/0213226 | A1* | 7/2016 | Yanagidate | A61B 1/045 |
| 2017/0035272 | A1 | 2/2017 | Endo | |
| 2017/0289523 | A1* | 10/2017 | Lee | H04N 13/207 |
| 2018/0047165 | A1* | 2/2018 | Sato | G06T 7/74 |
| 2018/0256018 | A1* | 9/2018 | Kobayashi | A61B 1/045 |
| 2019/0357758 | A1* | 11/2019 | Malinskiy | A61B 1/0669 |
| 2021/0045621 | A1* | 2/2021 | Bae | G06T 7/11 |
| 2021/0143996 | A1* | 5/2021 | Kawasaki | H04L 9/088 |
| 2021/0166354 | A1* | 6/2021 | Veit | G06T 5/70 |
| 2024/0347926 | A1* | 10/2024 | Joung | B32B 7/12 |

FOREIGN PATENT DOCUMENTS

| | | |
|---|---|---|
| JP | 4295948 B2 | 7/2009 |
| JP | 6395445 B2 | 9/2018 |
| JP | 6711595 B2 | 6/2020 |
| KR | 1020120069794 A | 6/2012 |
| KR | 10-1974719 B1 | 5/2019 |
| KR | 10-1977181 B1 | 5/2019 |
| KR | 10-2147974 B1 | 8/2020 |

OTHER PUBLICATIONS

International Search Report for PCT/KR2021/018163 dated Mar. 15, 2022 [PCT/ISA/210].

Korean Office Action for 10-2020-0168733 dated Jul. 26, 2022.

Korean Office Action for 10-2020-0168733 dated Mar. 10, 2023.

Communication dated Dec. 22, 2025 issued by the State Intellectual Property Office of the P.R.China in application No. 202180081580. X.

* cited by examiner

IMAGE DATA

603

START

TRANSMIT AND RECEIVE CONTROL SIGNALS BY
PERFORMING WIRELESS COMMUNICATION IN
FIRST FREQUENCY BAND — S606

GENERATE HDMI DATA BY FORMATTING AT LEAST
ONE IMAGE OBTAINED BY AT LEAST ONE CAMERA
ACCORDING TO HDMI FORMAT — S623

TRANSMIT IMAGE DATA TO EXTERNAL ELECTRONIC
DEVICE BY PERFORMING WIRELESS
COMMUNICATION IN SECOND FREQUENCY BAND — S641

END

| | FHD RESOLUTION | CAMERA RESOLUTION | NUMBER OF IMAGES |
|---|---|---|---|
| NUMBER OF PIXELS | 2073600 | 80000 | 25.92 |

FIG. 10C

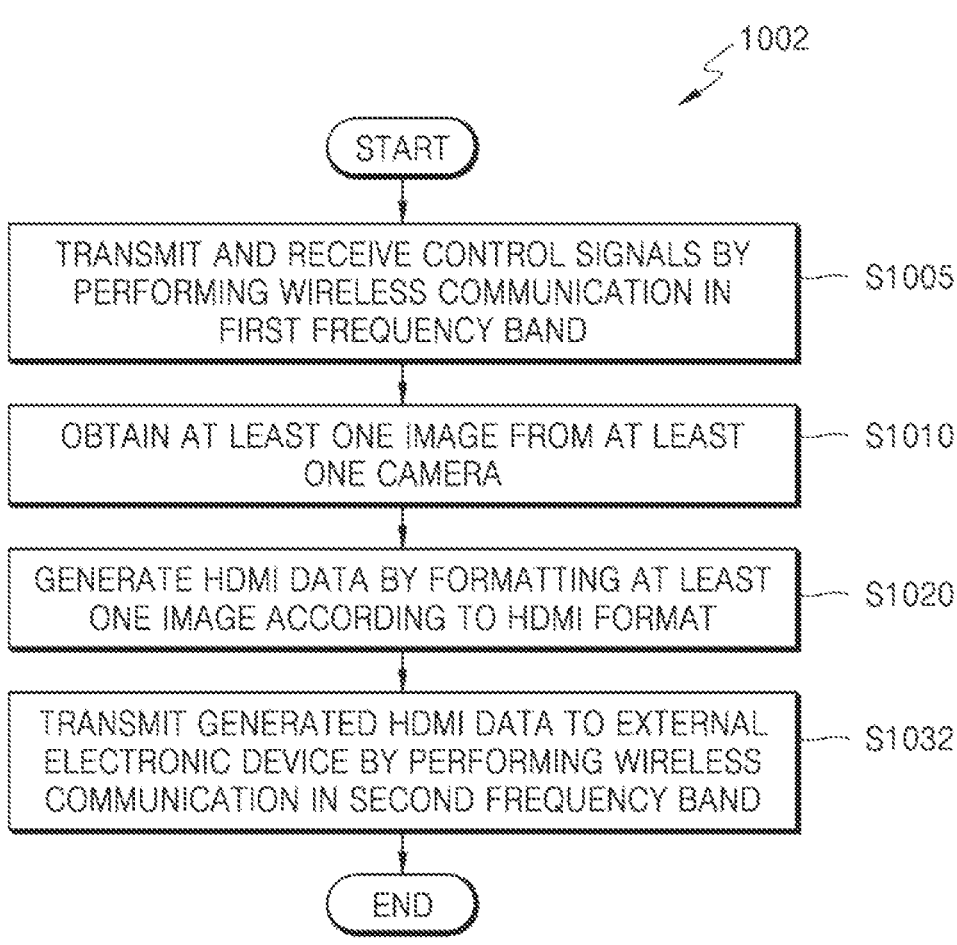

1002

START

TRANSMIT AND RECEIVE CONTROL SIGNALS BY PERFORMING WIRELESS COMMUNICATION IN FIRST FREQUENCY BAND — S1005

OBTAIN AT LEAST ONE IMAGE FROM AT LEAST ONE CAMERA — S1010

GENERATE HDMI DATA BY FORMATTING AT LEAST ONE IMAGE ACCORDING TO HDMI FORMAT — S1020

TRANSMIT GENERATED HDMI DATA TO EXTERNAL ELECTRONIC DEVICE BY PERFORMING WIRELESS COMMUNICATION IN SECOND FREQUENCY BAND — S1032

END

SCANNER FOR DENTAL TREATMENT, AND DATA TRANSMISSION METHOD OF SAME

TECHNICAL FIELD

The disclosed embodiments relate to a scanner and a data transmission method thereof.

Particularly, the disclosed embodiments relate to a scanner for transmitting at least one image obtained by the scanner for dental treatment to an external electronic device through wireless communication, and a data transmission method of the scanner.

BACKGROUND ART

There are various fields for dental treatment of patients. For dental treatment of a patient, it is important to accurately identify the state of the patient's oral cavity. In order to accurately identify the state of a patient's oral cavity, dental computer-aided design (CAD)/computer-aided manufacturing (CAM) technology is widely used.

In detail, the most important thing in dental treatment using CAD/CAM is to obtain precise three-dimensional data about the shape of the interior or exterior of an oral cavity, such as a patient's teeth, gums, or jawbone.

An intraoral scanner may be used to obtain three-dimensional data about an oral cavity. Three-dimensional optical scanners are widely used as intraoral scanners. The three-dimensional optical scanner may obtain images of an oral cavity by using light reflected from an object. Images obtained by the intraoral scanner may be transmitted to an external electronic device. Here, the external electronic device may be a computing device that processes the images obtained from the intraoral scanner to obtain three-dimensional data about the oral cavity, and may also be referred to as an oral diagnostic device.

The external electronic device needs to receive the images obtained from the intraoral scanner rapidly and without omission in order to obtain accurate three-dimensional data about the oral cavity.

Accordingly, there is a need to provide a method and device for rapidly and accurately transmitting, to an external electronic device, data including at least one image obtained from an intraoral scanner.

DESCRIPTION OF EMBODIMENTS

Technical Problem

The disclosed embodiments provide a scanner capable of rapidly and accurately transmitting data from the scanner to an external electronic device, and a data transmission method of the scanner.

In detail, the disclosed embodiments provide a scanner for dental treatment capable of transmitting a large amount of data from the scanner to an external electronic device rapidly and without omission, and a data transmission method of the scanner.

In addition, the disclosed embodiments provide a scanner for dental treatment capable of transmitting a large amount of data rapidly and without omission while increasing communication and control safety between the scanner and an external electronic device, and a data transmission method of the scanner.

Solution to Problem

A scanner for dental treatment according to an embodiment of the present disclosure includes: a camera module configured to obtain image data corresponding to at least one image; a communication unit including a first communication module configured to perform wireless communication in a first frequency band, and a second communication module configured to perform wireless communication in a second frequency band; and a processor configured to execute at least one instruction. Here, the processor performs control such that control signals related to at least one of operations of obtaining and transmitting the at least one image are transmitted to and received from an external electronic device through the first communication module performing the wireless communication in the first frequency band, and performs control such that the image data is transmitted to the external electronic device through the second communication module performing the wireless communication in the second frequency band.

In addition, the camera module may include: at least one camera configured to obtain the at least one image; and a camera board configured to obtain the image data corresponding to the at least one image.

A scanner for dental treatment according to an embodiment of the present disclosure includes: a camera module comprising at least one camera; a communication unit including a first communication module configured to perform wireless communication in a first frequency band, and a second communication module configured to perform wireless communication in a second frequency band; and a processor configured to execute at least one instruction. Here, the processor obtains image data corresponding to at least one image obtained by the at least one camera, performs control such that control signals related to at least one of operations of obtaining and transmitting the at least one image are transmitted to and received from an external electronic device through the first communication module performing wireless communication in the first frequency band, and performs control such that the image data is transmitted to the external electronic device through the second communication module performing wireless communication in the second frequency band.

In addition, the second communication module may perform wireless communication in the second frequency band that is a frequency band different from the first frequency band.

In addition, the processor may receive the control signal regarding a setting of the at least one camera from the external electronic device through the first communication module, and control the at least one camera to obtain the at least one image based on the control signal.

In addition, the scanner according to an embodiment of the present disclosure may further include a light emission unit configured to output light to be imaged with an object. In addition, when the control signal for requesting image scanning is received from the external electronic device through the first communication module, the processor may perform control such that a trigger signal for synchronizing the outputting of the light with the image scanning is output from the light emission unit to the at least one camera.

In addition, the scanner according to an embodiment of the present disclosure may further include a light emission unit configured to output light to be imaged with an object. In addition, when a control signal for controlling at least one of an output timing and an output intensity of the light is received from the external electronic device through the first communication module, the processor may control the light emission unit based on the control signal.

In addition, the scanner according to an embodiment of the present disclosure may further include a light emission unit configured to output light toward the object. In addition, the at least one camera may obtain at least one image based on driving of a lens. In addition, when the control signal for requesting image scanning is received from the external electronic device through the first communication module, the processor may perform control such that a trigger signal for synchronizing the driving of the lens with the image scanning is output to the at least one camera.

In addition, the second frequency band may be a frequency band that is higher than the first frequency band.

In addition, the first communication module may perform two-way wireless communication between the intraoral scanner and the external electronic device in the first frequency band, and the second communication module may perform one-way wireless communication from the intraoral scanner to the external electronic device in the second frequency band.

In addition, the control signals may include at least one of a signal regarding starting of photographing by the at least one camera, a signal regarding a setting of a region of interest (ROI) of the at least one camera, a signal regarding an image pixel setting of the at least one camera, a signal regarding a frame rate setting of the at least one camera, a signal regarding a gain setting of the at least one camera, a signal regarding an exposure time setting of the at least one camera, a signal regarding an output intensity of light output from a projector, a signal regarding an output timing of the light output from the projector, a signal regarding communication connection of the intraoral scanner, a signal for requesting transmission of the image data, a signal regarding a mode setting of the intraoral scanner, and a signal regarding termination of photographing by the intraoral scanner.

In addition, the scanner according to an embodiment of the present disclosure may further include a user interface configured to receive a user input, and the control signals may include a signal including a request or a command corresponding to the user input.

In addition, each of the at least one camera may obtain an image having a first resolution. In addition, the processor may obtain the image data obtained by formatting the at least one image into a frame image corresponding to a High-Definition Multimedia Interface (HDMI) format. In addition, the frame image may be a frame image having a second resolution that is higher than the first resolution.

In addition, the at least one camera may perform image capture at a first frame per second (FPS), and the image data may be a frame image corresponding to a second FPS that is less than the first FPS. In addition, the processor may control the second communication module to transmit the frame image to the external electronic device.

Advantageous Effects of Disclosure

A scanner for dental treatment and a data transmission method thereof according to embodiments of the present disclosure may enable transmission and reception of control signals required to control the scanner to obtain and/or transmit images, without interrupting transmission of image data.

BRIEF DESCRIPTION OF DRAWINGS

The present disclosure may be readily understood with a combination of the following detailed descriptions and the accompanying drawings, wherein reference numbers refer to structural elements.

FIG. 10C is another flow chart illustrating a data transmission method of an intraoral scanner according to an embodiment of the present disclosure.

MODE OF DISCLOSURE

Figure 1A:
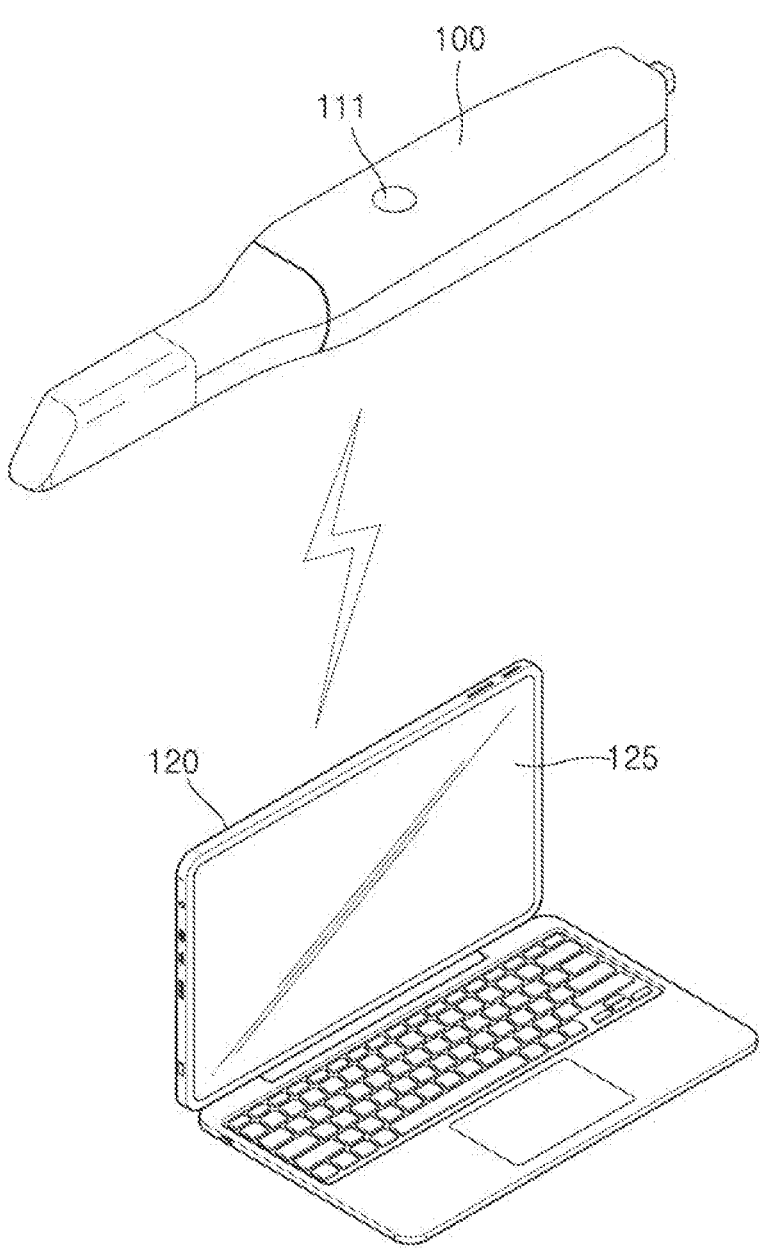
FIG. 1A is a diagram for describing an intraoral scanner and an external electronic device communicating with the intraoral scanner, according to an embodiment of the present disclosure.

The principle of the present disclosure is described and embodiments are disclosed in such a manner that the scope of the present disclosure becomes apparent and the present disclosure may be carried out by those of skill in the art to which the present disclosure pertains. The disclosed embodiments may be implemented in various forms.

Like reference numerals denote like elements throughout the present specification. The disclosed embodiments do not describe all elements of embodiments, and general content in the art to which the present disclosure pertains or identical content between the embodiments will be omitted. The terms "part" and "portion" as used herein may be embodied as software or hardware, and a plurality of "parts" may be embodied as a single unit or element, while a single "part" may include a plurality of elements, according to embodiments.

As used herein, the expression "configured to" may be interchangeably used with, for example, "suitable for", "having the capacity to", "designed to", "adapted to", "made to", or "capable of", according to a situation. The expression "configured to" may not imply only "specially designed to" in a hardware manner. Instead, in a certain circumstance, the expression "a system configured to" may indicate the system "capable of" together with another device or components. For example, "a processor configured (or set) to perform A, B, and C" may imply a dedicated processor (e.g., an embedded processor) for performing a corresponding operation or a generic-purpose processor (e.g., central processing unit (CPU) or an application processor) capable of performing corresponding operations by executing one or more software programs stored in a memory.

In the disclosed embodiments, a scanner refers to an electronic device for obtaining an image related to an object. In detail, the scanner may refer to a scanner for obtaining an image related to an oral cavity to be used for oral treatment. In addition, hereinafter, a 'scanner for oral treatment' may be referred to as an 'intraoral scanner' for convenience of description. For example, an intraoral scanner in the disclosed embodiments may be an intraoral scanner having a form that may be inserted into an oral cavity. Alternatively, the intraoral scanner in the disclosed embodiments may be a table-type scanner usable for dental treatment.

Hereinafter, for convenience of description, a scanner for dental treatment and a table-type scanner, which may be inserted into an oral cavity, will be collectively referred to as 'intraoral scanners'.

In the disclosed embodiments, an image may refer to an image representing an object included in an oral cavity (e.g., an 'intraoral image'). Here, the 'object' may include a tooth, gingiva, at least a partial region of an oral cavity, and/or an artificial structure insertable into an oral cavity (e.g., an orthodontic device including a bracket and a wire, an implant, an artificial tooth, dental fillings including inlays and onlays, an orthodontic auxiliary tool inserted into an oral cavity, etc.). Alternatively, the object may include an artificial object related to an oral cavity, for example, a plaster model, a crown, etc. In addition, the orthodontic device may include at least one of a bracket, an attachment, an orthodontic screw, a lingual orthodontic device, and a removable orthodontic retainer.

In addition, in the disclosed embodiments, an image may be a two-dimensional image of an object or a three-dimensional model or three-dimensional image representing an object in three dimensions.

In addition, in the disclosed embodiments, an image may refer to data required to represent an object in two dimensions or three dimensions, for example, raw data or a raw image obtained by at least one camera. In detail, the raw image is data obtained to generate an intraoral image necessary for diagnosis, and may be an image (e.g., a two-dimensional frame image) obtained by at least one camera included in the intraoral scanner when scanning the oral cavity of a patient, which is an object, by using the intraoral scanner. In addition, the raw image is an unprocessed image and may refer to an original image obtained by the intraoral scanner.

Hereinafter, embodiments will be described in detail with reference to the drawings.

FIG. 1A is a diagram for describing an intraoral scanner and an external electronic device communicating with the intraoral scanner, according to an embodiment of the present disclosure. First, with reference to FIG. 1A, an example will be described in which the scanner according to an embodiment of the present disclosure is an intraoral scanner having a shape insertable into an oral cavity.

Referring to FIG. 1A, an intraoral scanner 100 is a medical device for obtaining an intraoral image. A scanner having a shape insertable into an oral cavity, such as the intraoral scanner 100 illustrated in FIG. 1A, may be referred to as an intraoral scanner, a portable scanner, or the like.

In detail, the intraoral scanner 100 may be a device for generating a three-dimensional model of an oral cavity including at least one tooth, by being inserted into the oral cavity and scanning teeth in a contactless manner. In addition, the intraoral scanner 100 may have a shape capable of being drawn in and out of an oral cavity, and scans the oral cavity of a patient by using at least one camera (e.g., an optical camera, etc.). The intraoral scanner 100 may obtain, as raw data, surface information about an object, in order to image the surface of at least one of teeth, gingiva, an artificial structure (e.g., an orthodontic device including a bracket and a wire, an implant, an artificial tooth, an orthodontic auxiliary tool inserted into the oral cavity, etc.), and a plaster model.

Here, the raw data obtained by the intraoral scanner 100 may be at least one image obtained by at least one camera included in the intraoral scanner 100. raw data, the raw data may be at least one two-dimensional frame image obtained by the intraoral scanner 100 scanning the oral cavity. Here, the 'frame image' may be referred to as a 'frame' or 'frame data'.

The raw data obtained by the intraoral scanner 100 may be transmitted to an external electronic device 120 connected to the intraoral scanner 100 through a communication network.

In addition, the intraoral scanner 100 may obtain a three-dimensional model or a three-dimensional image generated based on the raw data obtained by the at least one camera. In addition, the obtained three-dimensional model or three-dimensional image may be transmitted to the external electronic device 120.

The external electronic device 120 may be connected to the intraoral scanner 100 through a communication network, and receive, from the intraoral scanner 100, the data obtained by scanning the oral cavity. The external electronic device 120 may be any electronic device capable of generating, processing, displaying, and/or transmitting an intraoral image based on data transmitted from the intraoral scanner 100.

In detail, the external electronic device 120 may generate at least one of information necessary for diagnosis of the oral cavity and an image representing the oral cavity, based on the data received from the intraoral scanner 100, and display the generated information and image on a display 125.

For example, the external electronic device 120 may be any electronic device capable of generating, processing, displaying, and/or transmitting three-dimensional data or a three-dimensional image of an object, based on image data received from the intraoral scanner 100.

The external electronic device 120 may be a computing device such as a smart phone, a laptop computer, a desktop computer, a personal digital assistant (PDA), or a tablet personal computer (PC), but is not limited thereto.

In addition, the external electronic device 120 may be in the form of a server (or a server device) or the like for processing an intraoral image.

In addition, the external electronic device 120 may store and execute dedicated software linked to the intraoral scanner 100. Here, the dedicated software may be referred to as a dedicated program or a dedicated application. In a case in which the external electronic device 120 operates in conjunction with the intraoral scanner 100, the dedicated software stored in the external electronic device 120 may be connected to the intraoral scanner 100 to receive in real time data obtained through object scanning. In an embodiment, there may be dedicated software for each intraoral scanner product for processing data. The dedicated software may perform at least one operation for obtaining, processing, storing, and/or transmitting a three-dimensional image of an object.

In addition, the intraoral scanner 100 may transmit raw data obtained through oral cavity scanning, to the external electronic device 120 as it is. Then, the external electronic device 120 may generate a three-dimensional intraoral image representing the oral cavity in three dimensions, based on the received raw data. In addition, because the intraoral scanner 100 may generate the 'three-dimensional intraoral image' by modeling the internal structure of the oral cavity in three dimensions based on the received raw data, data generated in this way may be referred to as a 'three-dimensional intraoral model'.

Hereinafter, an example in which the scanner according to an embodiment of the present disclosure is a table-type scanner that may be placed on a table or the like rather than being inserted into an oral cavity will be described with reference to FIG. 1B.

Figure 1B:
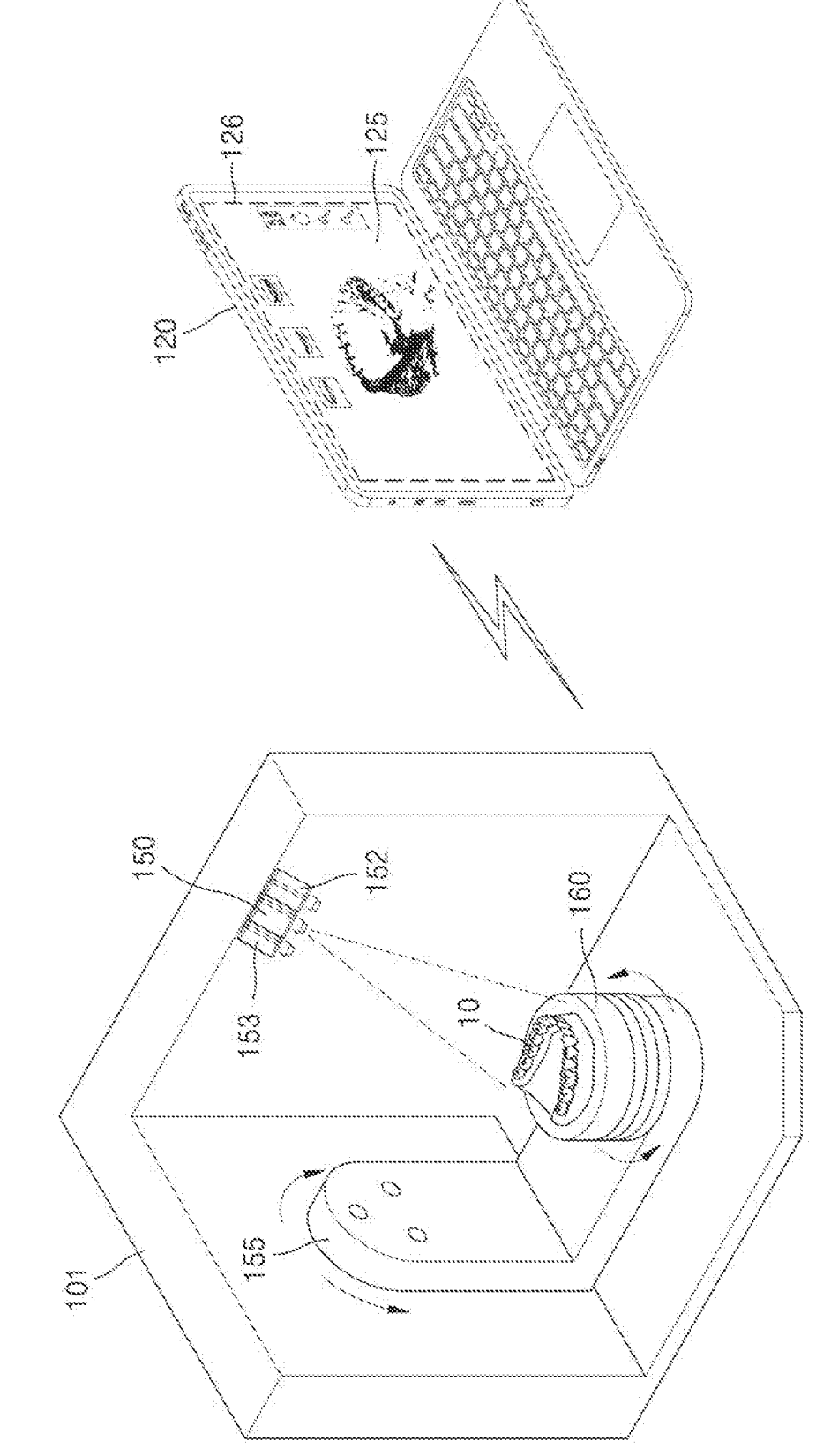
FIG. 1B is a diagram for describing an intraoral scanner and an external electronic device communicating with the intraoral scanner, according to an embodiment of the present disclosure.

FIG. 1B is a diagram for describing an intraoral scanner and an external electronic device communicating with the intraoral scanner, according to an embodiment of the present disclosure. In FIG. 1B, the same elements as those of FIG. 1A are illustrated with the same reference numerals.

Referring to FIG. 1B, an intraoral scanner 101 according to an embodiment of the present disclosure is a scanner that obtains an image related to an oral cavity to be used for oral treatment as described above, and may be a table-type scanner.

The intraoral scanner 101 may obtain three-dimensional data representing the shape of an object, by projecting light onto the object and scanning the object onto which the light is projected, by using the principle of triangulation by pattern deformation. The method of obtaining the three-dimensional data is not limited thereto, and various known scan methods may be applied.

Referring to FIG. 1B, the intraoral scanner 101 may include one or more cameras 152 and 153, a light emission unit 150, a turntable 160, and an arm 155.

The intraoral scanner 101 may obtain raw data by scanning an object. In an embodiment, the intraoral scanner 101 may project light onto an object 10 positioned on the turntable 160, through the light emission unit 150. The light output from the light emission unit 150 may have various shapes, such as a line or dot shape, a structured light shape, or a stripe pattern.

In addition, the light emission unit 150 may itself generate light whose pattern changes. For example, the light emission unit 150 may be a projector or the like that outputs light through a light source.

Alternatively, the light emission unit 150 may output light having a certain intensity, and the light output from the light emission unit 150 may be transformed into light having a certain pattern while passing through a pattern generation device (not shown).

Hereinafter, for convenience of description, an example will be described in which the light emission unit 150 included in the intraoral scanner 101 is a 'projector'.

The intraoral scanner 101 may obtain image data about the object by scanning the surface of the object onto which the light is projected, by using the one or more cameras 152 and 153 (e.g., optical cameras). Here, the 'image data' may refer to a plurality of two-dimensional images obtained by scanning the surface of the object by using the one or more cameras 152 and 153 in order to generate three-dimensional data about the object. In this case, the image data may be raw data. Alternatively, image data obtained by the intraoral scanner 101 may be a three-dimensional image representing the object in three-dimensional by using two-dimensional images.

The intraoral scanner 101 may include at least one camera as described above, and FIG. 1B illustrates an example in which the intraoral scanner 101 includes two cameras 152 and 153. Accordingly, in an embodiment, the intraoral scanner 101 may include one camera, or may include three or more cameras.

In an embodiment, the intraoral scanner 101 may obtain image data including a plurality of two-dimensional image frames by using a plurality of cameras 152 and 153 to scan the object. For example, the intraoral scanner 101 may obtain a plurality of two-dimensional images by projecting light onto the object through the light emission unit 150 and scanning the object onto which the light is projected.

The turntable 160 may be connected to the housing of the intraoral scanner 101 through the arm 155. The turntable 160 may be moved or rotated along a preset moving path. In an embodiment, the turntable 160 may swing in an axial direction under control by the arm 155 or may be rotated by a preset angle with respect to the central axis. In an embodiment, the turntable 160 may be stopped for a preset time period after moving or rotating once for a unit movement time period.

The intraoral scanner 101 and the external electronic device 120 may be connected to each other through a wireless communication network. For example, the intraoral scanner 101 may communicate with the external electronic device 120 through a wireless communication network according to a communication standard such as Bluetooth, Wi-Fi, Bluetooth Low Energy (BLE), near-field communication (NFC)/radio-frequency identification (RFID), Wi-Fi Direct, ultra-wideband (UWB), or Zigbee.

The intraoral scanner 101 may transmit the obtained image data to the external electronic device 120.

As described with reference to FIG. 1A, the external electronic device 120 may store and execute dedicated software. For example, the dedicated software may be stored in a processor (not shown) or a memory (not shown) of the external electronic device 120. In addition, the dedicated software may provide a user interface for use of data obtained from the intraoral scanner 101. A user interface screen 126 provided by the dedicated software may include a three-dimensional image of the object generated according to an embodiment of the present disclosure.

As described with reference to FIGS. 1A and 1B, in an embodiment of the present disclosure, the intraoral scanner 100 or 101 may scan an oral cavity by using an optical triangulation method, a confocal method, or the like.

In detail, the intraoral scanner 100 or 101 may obtain tens to thousands of images per second, and transmit the obtained images to the external electronic device 120 in real time. Here, in order for the external electronic device 120 to generate a three-dimensional model of the oral cavity in real time by using images obtained by the intraoral scanner 100 or 101, the intraoral scanner 100 or 101 needs to transmit hundreds of obtained images to the external electronic device 120 in real time without a delay.

An intraoral scanner and a data transmission method thereof according to embodiments of the present disclosure enable the intraoral scanner 100 or 101 to rapidly wirelessly transmit image data corresponding to the obtained raw data to the external electronic device 120. A detailed configuration and operations of the intraoral scanner and the data transmission method thereof according to embodiments of the present disclosure will be described in detail below with reference to the accompanying drawings.

In addition, in the drawings and detailed descriptions below, for convenience of description, an example will be described in which the intraoral scanner 100 according to an embodiment of the present disclosure is the intraoral scanner 100 having a shape insertable into an oral cavity as illustrated in FIG. 1A.

Figure 2A:
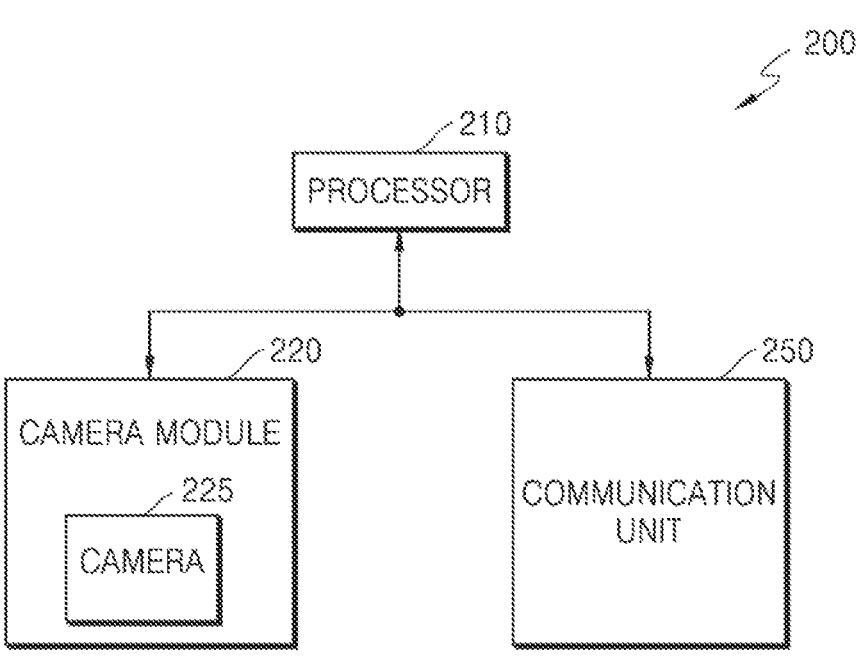
FIG. 2A is a block diagram illustrating an intraoral scanner according to an embodiment of the present disclosure.

FIG. 2A is a block diagram illustrating an intraoral scanner according to an embodiment of the present disclosure. An intraoral scanner 200 according to an embodiment of the present disclosure corresponds to the intraoral scanners 100 and 101 described above with reference to FIGS. 1A and 1B, and thus, redundant descriptions provided above with reference to FIGS. 1A and 1B will be omitted.

Referring to FIG. 2A, the intraoral scanner 200 includes a camera module 220, a communication unit 250, and a processor 210.

The camera module 220 may include at least one camera, and may obtain at least one image by photographing an oral cavity. In detail, the camera module 220 may include at least one camera, and may generate image data to be transmitted to an external electronic device (not shown) (e.g., corresponding to 120 of FIG. 1A) by photographing the oral cavity.

Here, the image data generated by the camera module 220 may be at least one image obtained by the at least one camera.

Alternatively, the camera module 220 may generate image data corresponding to at least one image obtained by the at least one camera. Alternatively, the camera module 220 may generate image data by modifying the configuration of at least one image obtained by the at least one camera. Alternatively, the image data generated by the camera module 220 may be a three-dimensional image or a three-dimensional model representing an object in three dimensions based on a plurality of images obtained by the at least one camera. Hereinafter, for convenience of description, 'at least one camera 225' will be referred to as a 'camera 225'. That is, the camera 225 may refer to one camera or may refer to a plurality of cameras.

The camera 225 includes at least one image sensor (not shown). In detail, each of the at least one camera included in the camera 225 may include a lens (not shown) and an image sensor (not shown). Here, the image sensor (not shown) may be a device that converts light entering the lens (not shown) into an electrical signal to display an image, in order to obtain the image.

The camera 225 may obtain hundreds of images per second according to a set frame per second (FPS). Here, the image obtained by the camera 225 may be a two-dimensional frame image. The FPS indicates the number of frame images obtained per second, and may also be referred to as a 'frame rate'.

For example, when the FPS at which the camera 225 operates is 100 FPS, the camera 225 may obtain 100 intraoral images per second. For example, in a case in which the camera 225 of the intraoral scanner 200 includes two cameras including an R camera and an L camera, each of the R camera and the L camera obtains 100 images per second. In addition, because the R camera and the L camera operate in synchronization with each other, the R camera and the L camera may obtain an R image and an L image, respectively, at every time point.

As another example, in a case in which the camera 225 of the intraoral scanner 200 includes one camera, 100 images may be obtained per second.

As another example, in a case in which the intraoral scanner 200 performs image scanning in a confocal manner, each of at least one camera included in the camera 225 may include a lens (not shown) to be movable to adjust the position of a focal point, and an image sensor (not shown) configured to obtain an image based on light having passed through the lens (not shown).

The communication unit 250 may perform wireless communication with an external electronic device (not shown in FIG. 2) (e.g., 120 of FIG. 1A) through a plurality of communication channels. Here, the communication channel may refer to a communication network for transmitting and receiving radio signals through a certain frequency band. In detail, the communication channel may be a communication network for transmitting and receiving radio signals of a frequency band defined according to a certain radio communication standard. Here, the wireless communication standard may be a communication standard such as Wireless Gigabit (WiGig), Bluetooth, Wi-Fi, BLE, NFC/RFID, Wi-Fi Direct, UWB, or ZIGBEE. In addition, a communication network of a certain frequency band or conforming to a certain communication standard may be referred to as a communication channel.

In addition, the communication unit 250 may also perform wired communication with an external electronic device (not shown). However, in an embodiment of the present disclosure, an example will be illustrated and described in which the communication unit 250 performs wireless communication with the external electronic device (not shown).

The processor 210 may perform an intended operation by executing at least one instruction. In detail, the processor 210 may control an operation of photographing (or scanning) an oral cavity, an operation of obtaining an image of the oral cavity, and/or an operation of transmitting data corresponding to the obtained image. In addition, when it is described that the processor 210 performs a certain operation, this may mean that the processor 210 directly performs the above-described operations by executing at least one instruction, as well as that the processor 210 controls other components such that the above-described operations are performed.

In detail, the processor 210 may include random-access memory (RAM) (not shown), which stores signals or data input from a source external to the intraoral scanner 200 or is used as a storage for various operations performed by the intraoral scanner 200, read-only memory (ROM) (not shown) storing a control program and/or a plurality of instructions for controlling the intraoral scanner 200, and at least one processor (hereinafter, referred to as an 'internal processor') (not shown) configured to execute at least one instruction. In detail, the processor 210 may be implemented to include at least one internal processor and a memory device (e.g., RAM, ROM, etc.) for storing at least one of programs, instructions, signals, and data to be processed or used by the internal processor.

Also, the processor 210 may include a graphics processing unit (GPU) (not shown) for graphics processing on a video. In addition, the processor 210 may be implemented as a system-on-chip (SoC) in which a core (not shown) and a GPU (not shown) are integrated. In addition, the processor 210 may include a single processor core (single-core) or a plurality of processor cores (multi-core). For example, the processor 210 may be dual-core, triple-core, quad-core, hexa-core, octa-core, deca-core, dodeca-core, hexadecimal-core, or the like.

In addition, the processor 210 may include a field-programmable gate array (FPGA), which is a semiconductor device including a designable logic device and a programmable internal circuit, and may perform high-speed image processing by using the FPGA.

Figure 2B:
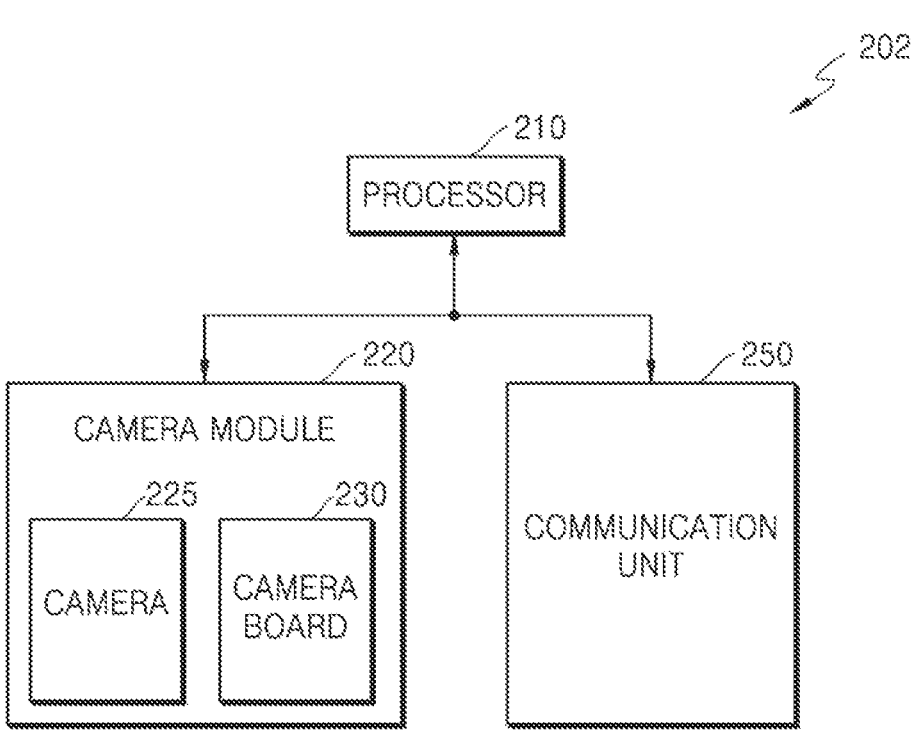
FIG. 2B is another block diagram illustrating an intraoral scanner according to an embodiment of the present disclosure.

FIG. 2B is another block diagram illustrating an intraoral scanner according to an embodiment of the present disclosure. An intraoral scanner 202 according to an embodiment of the present disclosure corresponds to the intraoral scanner 200 illustrated in FIG. 2A, and the same components are illustrated by using the same reference numerals. Thus, in describing the intraoral scanner 202, the descriptions provided above with reference to FIG. 2A will be omitted.

In detail, the camera module 220 may obtain image data corresponding to at least one image. In detail, the camera module 220 of the intraoral scanner 202 may include the at least one camera 225 configured to obtain at least one image, and a camera board 230 configured to obtain image data corresponding to the at least one image.

In addition, the camera board 230 may control the camera 225 for image scanning. For example, the camera board 230 may set a region of interest (ROI), an exposure time, and/or a frame rate of the camera 225.

Alternatively, the camera board 230 may generate image data corresponding to at least one image obtained by the camera 225. For example, the camera board 230 may generate the image data corresponding to the at least one image obtained by the camera 225 by converting the format of the at least one image.

In addition, in a case in which the camera module 220 does not include the camera board 230 as illustrated in FIG. 2A, at least one of the operations performed by the camera board 230 may be performed by the processor 210.

Figure 2C:
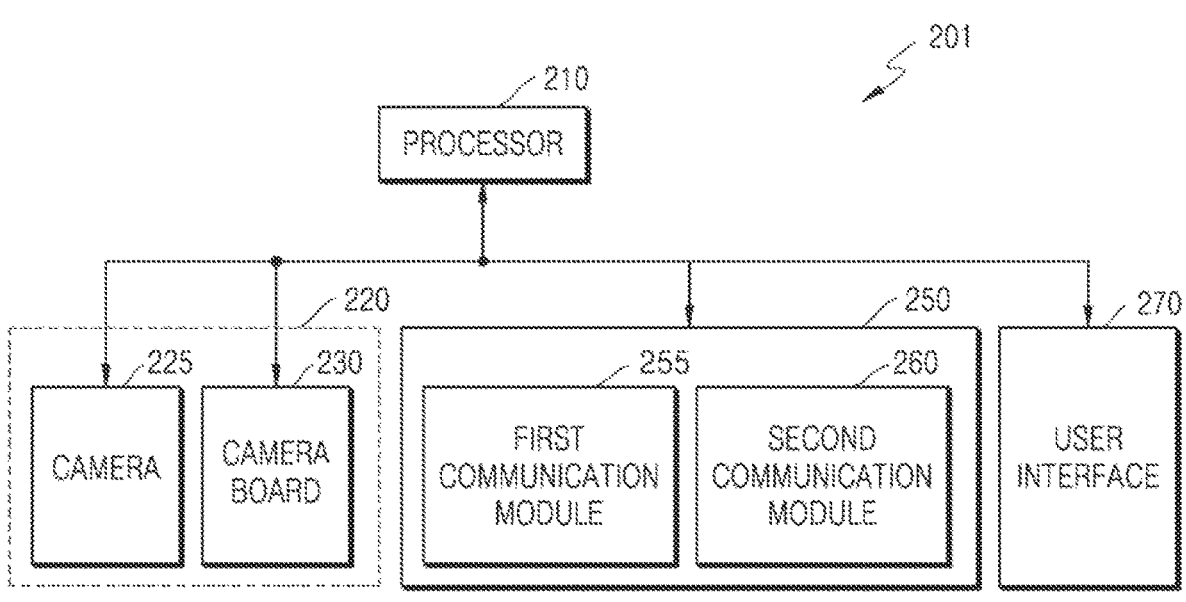
FIG. 2C is another block diagram illustrating an intraoral scanner according to an embodiment of the present disclosure.

FIG. 2C is another block diagram illustrating an intraoral scanner according to an embodiment of the present disclosure. In detail, an intraoral scanner 201 illustrated in FIG. 2C represents a detailed embodiment of the intraoral scanner 200 illustrated in FIG. 2A, and the same components of FIG. 2C as the components of FIGS. 2A and 2B are illustrated with the same reference numerals. Thus, in describing the intraoral scanner 201, redundant descriptions provided above with reference to FIGS. 1A to 2B will be omitted.

Referring to FIG. 2C, the intraoral scanner 201 includes the camera module 220, the communication unit 250, and the processor 210. In addition, the intraoral scanner 201 may further include a light emission unit (not shown) configured to output light to be imaged with an object. The light emission unit (not shown) may correspond to the light emission unit 150 described above with reference to FIG. 1B, and may correspond to a light emission unit 284 of FIG. 2D to be described below.

In the intraoral scanner 201, the camera module 220 may correspond identically to the camera module 220 illustrated in FIGS. 2A and 2B and described above. An example in which the camera module 220 includes the camera board 230 as illustrated in FIG. 2B will be described with reference to FIG. 2C.

In an embodiment of the present disclosure, the intraoral scanner 201 is a scanner for dental treatment, and includes the at least one camera 225, the communication unit 250 including a first communication module 255 configured to perform wireless communication in a first frequency band and a second communication module 260 configured to perform wireless communication in a second frequency band, and the processor 210 configured to execute at least one instruction. Here, the processor 210 obtains image data corresponding to at least one image obtained by the at least one camera 225, performs control such that control signals related to at least one of operations of obtaining and transmitting the at least one image are transmitted to and received from an external electronic device through the first communication module 255 performing wireless communication in the first frequency band, and performs control such that the image data is transmitted to the external electronic device through the second communication module 260 performing wireless communication in the second frequency band.

In addition, the second frequency band may be a frequency band different from the first frequency band. That is, the second communication module 260 may perform wireless communication in the second frequency band that is different from the first frequency band.

Hereinafter, detailed operation examples of the intraoral scanner 201 will be described.

The intraoral scanner 201 may control an image scanning operation for obtaining at least one image, based on a control signal transmitted through the first communication module 255.

In detail, the camera 225 may perform an oral cavity scanning operation under control by the processor 210. For example, the camera 225 may set necessary settings for oral cavity scanning, based on a control signal transmitted from the processor 210.

For example, the camera 225 may set a ROI of the camera under control by the processor 210. Alternatively, the camera 225 may set image pixels of the camera under control by the processor 210. Alternatively, the camera 225 may set the frame rate of the camera under control by the processor 210. Alternatively, the camera 225 may set the gain of the camera under control by the processor 210. Alternatively, the camera 225 may set the exposure time of one camera under control by the processor 210.

In addition, the camera 225 may perform an oral cavity scanning operation under control by the camera board 230. In detail, the camera 225 may set necessary settings for oral cavity scanning, based on a control signal transmitted from the camera board 230. In detail, the camera board 230 may have a built-in FPGA module. In this case, the FPGA module (not shown) may perform control related to digital signal processing and/or scanning operation of the camera. Accordingly, the camera 225 may perform an oral cavity scanning operation under control by the FPGA module (not shown).

For example, the camera 225 may set a ROI of the camera under control by the camera board 230 (e.g., the FPGA module (not shown)). Alternatively, the camera 225 may set image pixels of the camera under control by the camera board 230 (e.g., the FPGA module (not shown)). Alternatively, the camera 225 may set the frame rate of the camera under control by the camera board 230 (e.g., the FPGA module (not shown)). Alternatively, the camera 225 may set the gain of the camera under control by the camera board 230 (e.g., the FPGA module (not shown)). Alternatively, the camera 225 may set the exposure time of one camera under control by the camera board 230 (e.g., the FPGA module (not shown)).

In addition, the camera board 230 may generate image data corresponding to a plurality of images obtained by the camera 225 by converting the format of the plurality of images. Here, the converting of the format may mean modifying the format or shape of an image frame without compressing data. In detail, it may mean converting the plurality of images obtained by the camera 225 into image frames having a resolution different from that of the camera 225. In detail, the camera board 230 may format the plurality of images obtained by the camera 225 into image frames having a higher resolution than the resolution of the camera 225.

For example, the camera board 230 may format the plurality of images obtained by the camera 225 into frame images corresponding to a High-Definition Multimedia Interface (HDMI) format, and output the frame images. Here, the frame images generated by the formatting are data having the HDMI format, and thus may be referred to as 'HDMI data'. In detail, the camera board 230 may perform a formatting operation under control by the processor 210.

Here, the formatting may mean modifying the format of data without data loss.

Alternatively, the camera board 230 may compress (encode) at least one image obtained by the camera 225 to generate image data corresponding to a plurality of images.

In addition, each of at least one image obtained by at least one image sensor (not shown) included in the camera 225 may be a two-dimensional frame with M horizontal pixel values and N vertical pixel values (where M and N are natural numbers). Here, (M, N) may be set to various values according to product specifications of the camera 225, such as (100, 100), (200, 200), or (300, 300). In addition, the values of M and N may be different from each other. The camera 225 may obtain tens to thousands of two-dimensional frames per second according to the set frame rate.

In addition, the camera module 220 may further include a light emission unit (not shown) configured to output light, and the light emission unit (not shown) may output light to an object. In addition, the camera module 220 may obtain an image by performing image scanning on the object to which the light is emitted. In addition, the light emission unit (not shown) may be included in the intraoral scanner 201 as a separate component from the camera module 220, rather than being included in the camera module 220. Hereinafter, for convenience of description, an example in which the light emission unit (not shown) is included in the camera module 220 will be illustrated and described. Here, the light output from the light emission unit (not shown) may be generated and output to have various shapes by using various light sources. The light may be generated in a dot, line, or stripe pattern, or may be generated in the form of structured light. Alternatively, the light output from the light emission unit (not shown) may be transformed into light having a certain pattern and output while passing through a pattern generation device (not shown).

In addition, the light output from the light emission unit (not shown) may be referred to as a 'beam'. That is, the light output from the light emission unit (not shown) may be output toward the object in various shapes such as a dot pattern, a stripe pattern, or a structured light shape.

For example, the camera module 220 may perform oral cavity scanning by using an optical triangulation method. Here, the optical triangulation method refers to a scanning technique in which a light source (e.g., a pattern beam, etc.) is emitted toward an object to be scanned, and three-dimensional depth information is obtained by using the light source reflected from the object.

As another example, the camera module 220 may perform oral cavity scanning by using a confocal method. Here, the confocal method may also be referred to as a confocal scanning method. The confocal method refers to a scanning technique in which, when light output from the light emission unit (not shown) is reflected from an object, only information about light that is in focus is detected from among light reflected from the object to generate an image. In detail, in the confocal method, the position of a lens (e.g., an objective lens) may be moved to adjust the position of a focal point, and driving of the lens may be accompanied for image scanning.

In an embodiment of the present disclosure, the communication unit 250 may communicate with an external electronic device (not shown) through at least two communication channels.

In the intraoral scanner 201 according to an embodiment, the camera board 230 generates image data corresponding to a plurality of images obtained by the camera 225. In addition, the communication unit 250 may include the first communication module 255 configured to perform wireless communication in a first frequency band, and the second communication module 260 configured to perform wireless communication in a second frequency band that is different from the first frequency band. In addition, the processor 210 may execute at least one instruction to perform control such that control signals related to at least one of operations of obtaining and transmitting the plurality of images are transmitted to and received from the external electronic device (not shown) through the first communication module 255 performing wireless communication in the first frequency band. In addition, the processor 210 may perform control such that the image data generated by the camera board 230 is transmitted to the external electronic device (not shown) through the second communication module 260 performing wireless communication in the second frequency band.

In detail, the communication unit 250 includes the first communication module 255 configured to perform wireless communication in the first frequency band, and the second communication module 260 configured to perform wireless communication in the second frequency band that is different from the first frequency band. In detail, the second frequency band may be a higher frequency band than the first frequency band.

In detail, the first communication module 255 may transmit and receive control signals to and from the external electronic device (not shown).

Hereinafter, various examples of control signals transmitted and received through the first communication module 255 will be described in detail.

For example, the control signal may be a signal for controlling the operation of the camera 225 received from the external electronic device. For example, the control signal may be a signal for requesting image scanning. Here, the image scanning may refer to an operation of obtaining (or capturing) an image of an object by photographing the object.

In detail, when a control signal for requesting image scanning is received from the external electronic device (not shown) through the first communication module 255, the processor 210 may perform control such that a trigger signal for synchronizing light output by the light emission unit (not shown) with the image scanning is output from the light emission unit (not shown) to the camera 225. In detail, in a case in which the intraoral scanner 201 performs image scanning by using the optical triangulation method, the light emission unit (not shown) may be a projector (not shown). For example, the processor 210 may receive a control signal for requesting image scanning, from the external electronic device (not shown) through the first communication module 255. Then, in response to the received control signal, the processor 210 transmits, to the light emission unit (not shown) (e.g., the projector (not shown) (e.g., a projector 283 to be described below with reference to FIG. 2D), a signal for requesting to stand by for the image scanning. When receiving the signal for requesting to stand by for the image scanning, the light emission unit (not shown) may output, to the camera 225, a trigger signal for synchronizing light output with the image scanning.

Here, the trigger signal may be output in response to the image scanning whenever the image scanning is performed. In detail, the projector (not shown) may output a trigger signal to the camera 225 immediately before the image scanning is performed. In addition, the projector (not shown) may output light after outputting the trigger signal. Then, the camera 225 may perform the image scanning in response to receiving the trigger signal. That is, the trigger signal may be a signal for synchronizing the light output by the projector (not shown) with the image scanning operation of the camera 225.

As another example, in a case in which the intraoral scanner 201 performs image scanning by using the confocal method, the light emission unit (not shown) outputs light toward an object, and the at least one camera 225 may obtain at least one image based on light transmitted through a lens (e.g., the above-described objective lens) that collects and outputs light reflected from the object. In the above example, when the control signal for requesting the image scanning is received from the external electronic device (not shown) through the first communication module 255, the processor 210 may perform control such that a trigger signal for synchronizing driving of the lens with the image scanning is output to the at least one camera 225. In detail, in a case in which an image is obtained by using the confocal method, the trigger signal may be a signal for synchronizing driving of the lens for focus adjustment with image obtaining by the camera 225. For example, the trigger signal may be a signal including information indicating the amount by which the lens has been moved for the image scanning and that the image scanning thus needs to be started.

As another example, the control signal may be a signal including settings, information, requests, and/or commands necessary for the intraoral scanner 201 to obtain an image of an oral cavity. As another example, the control signal may be a signal including settings, information, requests, and/or commands necessary for the intraoral scanner 201 to transmit the obtained image to the external electronic device (not shown).

In addition, the control signal may be a signal transmitted from the intraoral scanner 201 to the external electronic device (not shown), or may be a signal received by the intraoral scanner 201 from the external electronic device (not shown).

In detail, the control signal may include signals for i) setting a ROI of the camera 225, ii) setting image pixels of the camera 225, iii) setting the frame rate of the camera 225, iv) setting the gain of the camera 225, v) setting the exposure time of the camera 225, vi) setting the light emission unit (not shown) included in the camera 225 (e.g., in a case in which the light emission unit (not shown) is a projector, a time point at which the projector outputs a beam, a time period during which the beam is output, a beam pattern setting, etc.), vii) setting a protocol and/or a mode for communication connection between the intraoral scanner 200 and the external electronic device (not shown), viii) setting data transmission and reception between the intraoral scanner 200 and the external electronic device (not shown), and ix) controlling the driving or focal point of a lens included in the camera 225 performing the image scanning by using the confocal method.

In addition, the control signal may be received from an external medical device (not shown) through the first communication module 255 in order to control the operation of the light emission unit (not shown) (e.g., a projector). For example, the control signal may be a control signal for controlling at least one of the shape of light output from the light emission unit (not shown) (e.g., a projector), a timing of output the light, and the output intensity of the light. Here, the shape of the light may refer to the pattern or shape of the light output to an object.

For example, when a control signal for controlling at least one of the output timing and output intensity of the light is received from the external electronic device (not shown) through the first communication module 255, the processor 210 may control the light emission unit (not shown) (e.g., a projector) based on the received control signal. Accordingly, the light emission unit (not shown) (e.g., a projector) may output light having an output intensity adjusted based on the control signal, at an output timing adjusted based on the control signal.

In addition, the intraoral scanner 201 may further include a user interface 270. The user interface 270 may receive a user input.

For example, the user interface 270 may include an input device including keys corresponding to certain operations or requests. For example, the input device included in the user interface 270 may be formed as at least one button or a touch sensor. Alternatively, the user interface 270 may include a speech recognition sensor, and may receive a user voice, and recognize a user input corresponding to a certain operation or request based on the received user voice. Referring back to FIG. 1A, the user interface 270 included in the intraoral scanner 100 may be formed as a button 111. FIG. 1A illustrates an example in which the user interface 270 of the intraoral scanner 100 is formed as one button 111.

As another example, the user interface 270 may be formed as a touch pad. In detail, the user interface 270 may include a touch pad (not shown) coupled to a display panel (not shown). In this case, a user interface screen may be output on the display panel. In addition, when a certain command is input through the user interface screen, the touch pad may detect the input and transmit detected information to the processor 210. Then, the processor 210 may interpret the detected information to recognize and execute the certain command input by the user.

In detail, in a case in which the user interface 270 is formed as a touch pad, when the user touches a certain point on the user interface screen, the user interface 270 detects the position of the touched point. Then, the user interface 270 may transmit information about the detected position to the processor 210. Then, the processor 210 may recognize the user's request or command corresponding to a menu displayed at the detected position, and execute the recognized request or command.

Hereinafter, an example will be described in which the user interface 270 is formed as one button 111 as illustrated in FIG. 1A.

In an embodiment of the present disclosure, control signals transmitted to and received from the external electronic device (not shown) through the first communication module 255 may be generated in response to a user input. In detail, when a user input is received through the user interface 270, the processor 210 may transmit a control signal corresponding to the received user input, to the external electronic device (not shown).

For example, in a case in which the user interface 270 is formed as one button 111 as illustrated in FIG. 1A, a user input corresponding to a manipulation of the button 111 may correspond to at least one request according to the way the button 111 is pressed. For example, a user manipulation of the button 111 may be classified as a double-click, a long-click, a single-click, or a single-click for a short time period, and recognized as a request differently depending on the recognized type of user manipulation.

For example, when the user presses the button 111 once for a short time period, the processor 210 may recognize that a user input for requesting to start scanning of an object is received. In addition, when the user presses the button 111 once for a long time period (or longer than a set time period), the processor 210 may recognize that a user input for requesting to terminate the scanning of the object is received. Alternatively, when the user double-clicks the button 111, the processor 210 may recognize that a user input for requesting to transmit image data corresponding to obtained images to the external electronic device (not shown) is received.

In addition, the user interface 270 of the intraoral scanner 201 may include a plurality of buttons corresponding to a plurality of requests, respectively. In this case, a request corresponding to a selected button may be recognized.

As another example, different requests may be recognized considering of an operation state of the intraoral scanner 201 when a user manipulation of the button 111 is performed. For example, when the button 111 is single-clicked while the intraoral scanner 201 is performing scanning, such a user input may be recognized as a request corresponding to stopping of the scanning. In addition, when the button 111 is single-clicked for a short time period in a state in which the intraoral scanner 201 stops the scanning, such a user input may be recognized as a request corresponding to resumption of the scanning.

As described above, the processor 210 may generate a control signal corresponding to a received user input, and transmit the generated control signal to the external electronic device (not shown) through the first communication module 255. That is, the control signal may be a signal including a request or command corresponding to the user input received through the user interface 270.

In addition, a control signal corresponding to a user input received through the external electronic device (not shown) may be received from the external electronic device (not shown) through the first communication module 255.

In addition, the control signal may be generated by at least one of the processor 210 and the camera module 220, and then transmitted to the external electronic device (not shown) through the first communication module 255.

In addition, the second communication module 260 may transmit and receive radio signals in the form of a millimeter wave. Here, the millimeter wave refers to a radio signal having a wavelength of 1 to 10 millimeters. Accordingly, the second communication module 260 that transmits and receives millimeter waves may transmit and receive radio signals in a bandwidth of 30 GHz to 300 GHz. In detail, the second communication module 260 may rapidly transmit a large amount of image data by transmitting and receiving millimeter-wave radio signals.

In detail, the second communication module 260 may transmit and receive wireless signals of a frequency band according to WiGig. In detail, the first communication module 255 may transmit and receive wireless signals in a frequency band of 802.11ad of WiGig. Here, wireless communication through the Institute of Electrical and Electronics Engineers (IEEE) 802.11ad frequency band may be referred to as WiGig. In addition, WiGig may support a data transmission rate of up to 7 giga bits per second (Gbps). In addition, WiGig may stably perform wireless communication within a distance of 10 m or less when maximally supporting the intensity of a wireless signal transmitted through beamforming. In addition, WiGig may support transmission and reception of data encrypted by using an encryption algorithm, and in this case, may provide an improved security function. In detail, WiGig may provide an improved security function by using Galois/Counter Mode of the Advanced Encryption Standard (AES) encryption algorithm.

For example, the second communication module 260 may transmit data in a 60-GHz band by using a wireless communication network conforming to WiGig.

In detail, in an embodiment of the present disclosure, image data generated by the camera module 220 may be transmitted to the external electronic device (not shown) through the second communication module 260.

In detail, the first communication module 255 may perform two-way wireless communication. In detail, the first communication module 255 may be responsible for transmission and reception of control signals through a first communication network having a first frequency band. In addition, the second communication module 260 may transmit and receive radio signals having a frequency band higher than the first frequency band.

In detail, the first communication module 255 and the second communication module 260 may transmit and receive radio signals in the first frequency band and the second frequency band, respectively.

In detail, the first frequency band and the second frequency band may be different frequency bands. For example, the first frequency band may be a frequency band defined according to a communication standard such as Bluetooth, Wi-Fi, BLE, NFC/RFID, Wi-Fi Direct, UWB, or ZIGBEE.

For example, the first communication module 255 may transmit a control signal to the external electronic device (not shown) through a wireless communication network of the first frequency band, for example, a 2.4-GHz band. As another example, the first communication module 255 may transmit a control signal to the external electronic device (not shown) through a wireless communication network of the first frequency band, for example, a 5-GHz band. As another example, the first communication module 255 transmits a control signal to the external electronic device (not shown) through a wireless communication network having an Industrial, Scientific, and Medical (ISM) frequency band, for example, a 4000-MHz frequency band or a 900-MHz frequency band.

In addition, the first communication module 255 may receive a control signal from the external electronic device (not shown).

In addition, the second communication module 260 may perform one-way wireless communication or two-way wireless communication.

In detail, when fast transmission of image data is desired, the second communication module 260 may perform one-way wireless communication. For example, the second communication module 260 may perform one-way wireless communication from the intraoral scanner (e.g., 200 or 201) to the external electronic device (not shown) in a 60-GHz frequency band for fast transmission of image data.

As in the above example, in a case in which the second communication module 260 is responsible for only transmission of image data, a transmission operation is not delayed due to a reception operation. Accordingly, the second communication module 260 may rapidly transmit image data to the external electronic device (not shown) without a delay, by performing one-way wireless communication for only transmission. In addition, the first communication module 255 may perform two-way wireless communication such that a control signal necessary for controlling the intraoral scanner (e.g., 200 or 201) may be transmitted or received at any time regardless of transmission of image data. Accordingly, the transmission efficiency of the intraoral scanner may be increased, and the safety of a control operation may be improved by immediate transmission and reception of control signals.

In addition, image data to be transmitted from the intraoral scanner to the external electronic device (not shown) may be HDMI data formatted according to the HDMI standard. In detail, the camera board 230 may generate image data (specifically, HDMI data) by formatting the format of a plurality of images obtained by the camera 225 into frame images corresponding to an HDMI format. In addition, the second communication module 260 may transmit the HDMI data formatted according to the HDMI standard, to the external electronic device (not shown) in a 60-GHz band. Here, the HDMI data transmitted to the external electronic device (not shown) may include a plurality of images obtained by at least one image sensor (not shown) included in the camera 225. The formatting operation according to the HDMI standard will be described in detail below with reference to FIGS. 7 to 9.

In detail, the HDMI data to be transmitted to the external electronic device (not shown) may include pixel values included in the plurality of images obtained by the camera 225, and may be data having a format according to the HDMI standard.

In the above example, the intraoral scanner 201 formats the plurality of images obtained by the camera 225 into HDMI data, and transmits the HDMI data through a frequency band of 60 GHz, thereby transmitting a large amount of image data at high speed. Accordingly, the pixel values included in the images obtained by the camera 225 may be included, as original values, in the HDMI data, and thus transmitted without data compression or data loss.

In the above example, the image data obtained by the intraoral scanner 201 may be formatted according to the HDMI standard and then transmitted through the second frequency band, for example, a 60-GHz frequency band, and data other than the image data, for example, a control signal related to control of the operation of the intraoral scanner 200 may be transmitted through the first frequency band lower than the second frequency band, for example, a 2.4-GHz frequency band. Accordingly, a large amount of image data obtained by the intraoral scanner 201 may be rapidly transmitted, and the control signal related to control of the operation of the intraoral scanner 201 may be accurately transmitted and received simultaneously with the transmission of the image data, or at a time point different therefrom. In addition, by transmitting and receiving the control signal by using the first frequency band lower than the second frequency band, the safety of transmission of the control signal may be increased.

Figure 2D:
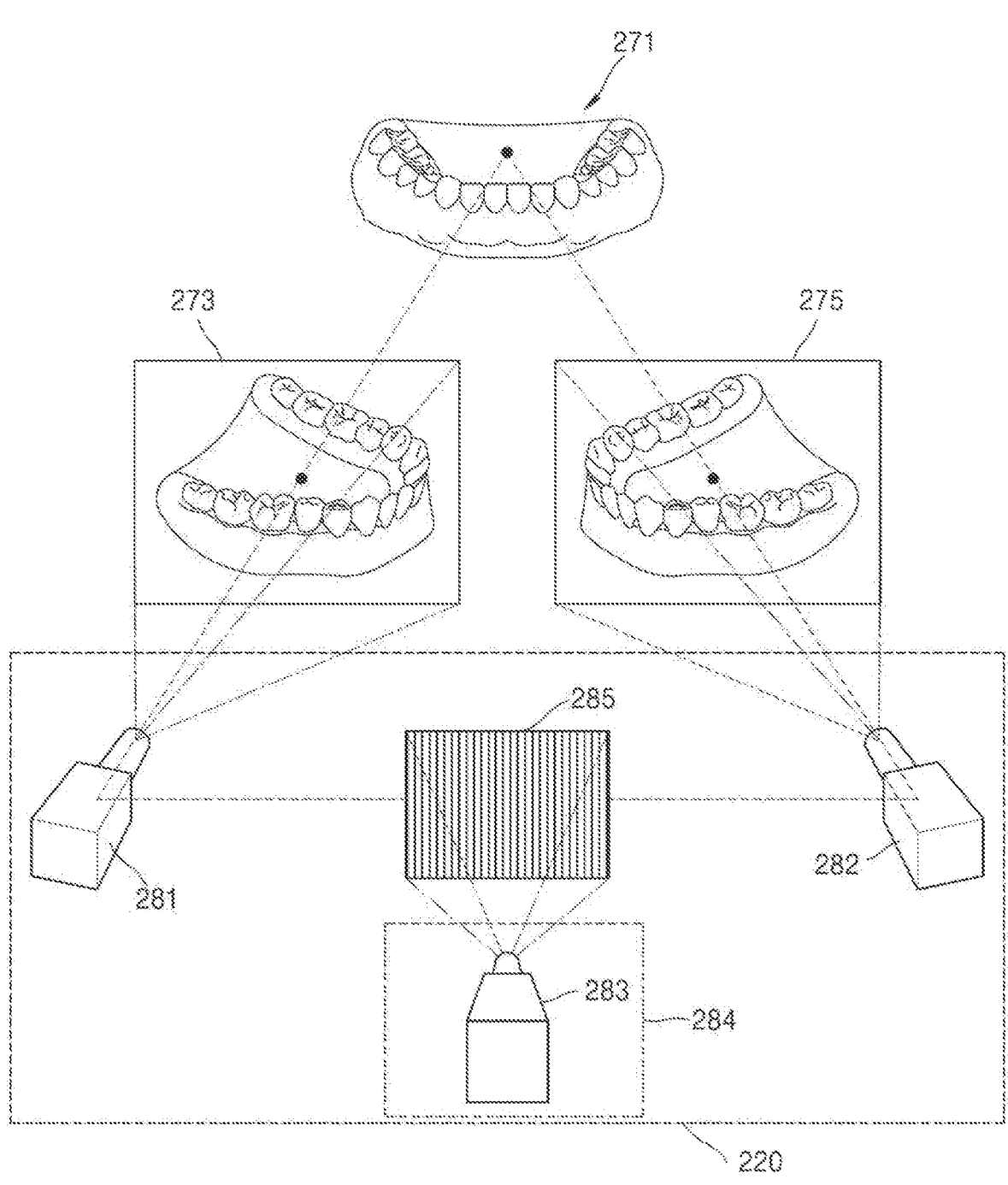
FIG. 2D is a diagram for describing an operation, performed by an intraoral scanner, of photographing an oral cavity, according to an embodiment of the present disclosure.

FIG. 2D is a diagram for describing an operation, performed by an intraoral scanner, of photographing an oral cavity, according to an embodiment of the present disclosure. In FIG. 2D, the same elements as those of FIG. 2C are illustrated by using the same reference numerals, and thus, redundant descriptions will be omitted. In addition, cameras 281 and 282 illustrated in FIG. 2D may correspond identically to the camera 225 illustrated in FIG. 2C.

In addition, FIG. 2D is a diagram illustrating a detailed embodiment of the camera module 220 included in the intraoral scanner 200, 201, or 202 according to an embodiment of the present disclosure. Hereinafter, with reference to FIG. 2D, an example in which the camera module 220 illustrated in FIG. 2D is included in the intraoral scanner 201 illustrated in FIG. 2C will be described.

As described above with reference to FIG. 2C, the camera 225 may include at least one camera. For example, the camera 225 may include one camera. As another example, the camera 225 may include two cameras. As another example, the camera 225 may include three or more cameras.

In detail, the camera 225 of the intraoral scanner 201 may be at least one camera configured to perform image scanning by using a confocal method, and may perform image scanning by moving (or driving) the position of a lens (e.g., an objective lens) included in a camera (not shown) by using the confocal method.

Alternatively, the camera 225 of the intraoral scanner 201 may be at least one camera configured to perform image scanning by using an optical triangulation method, and may perform image scanning on an object to which patterned light is emitted by using the optical triangulation method.

An example in which the camera 225 included in the intraoral scanner 201 includes two cameras 281 and 282 and performs image scanning by using the optical triangulation method is illustrated in and will be described with reference to FIG. 2D.

Referring to FIG. 2D, the intraoral scanner 201 may perform oral cavity scanning by using the optical triangulation method. In the optical triangulation method, three-dimensional data may be obtained by emitting light onto an object, then photographing the object, and using an image of the object imaged with the light. In detail, in the optical triangulation method, an image of an object may be obtained by emitting light onto the object and receiving the light reflected from the object. Here, the three-dimensional data may include three-dimensional depth information about the object.

In detail, in an embodiment of the present disclosure, a method based on structured light with stereo vision using two cameras and a projector that outputs light may be used to obtain three-dimensional data about the surface of an object.

For example, in order to perform scanning by using the method based on structured light with stereo vision, the camera module 220 may include the projector 283 and one or more cameras 281 and 282. Here, the cameras 281 and 282 include a lens and an image sensor to obtain an image by scanning or photographing an object. FIG. 2D illustrates an example in which the intraoral scanner 201 includes two cameras 281 and 282.

The intraoral scanner 201 may include the light emission unit 284. Here, the light emission unit 284 corresponds identically to the light emission unit 150 described above with reference to FIG. 1B, redundant descriptions provided above will be omitted.

The light emission unit 284 may be formed as the projector 283.

In detail, the projector 283 may output a beam having a pattern formed by at least one of a one-dimensional dot and a two-dimensional line. In detail, for oral cavity scanning, the projector 283 may output light into an oral cavity to be scanned, under control by the processor 210. When light is output from the projector 283, two or more cameras 281 and 282 may obtain images corresponding to the object onto which the light is projected. In addition, the shape (or pattern) of the light output from the projector 283 may be modified, and may have various configurations. FIG. 2D illustrates an example in which the projector 283 outputs structured light in the form of a plurality of lines.

Hereinafter, with reference to FIG. 2D, an example in which the camera module 220 according to an embodiment of the present disclosure includes the projector 283, the L camera 281, and the R camera 282 will be illustrated and described. In addition, an example in which the projector 283 outputs structured light 285 having a pattern as illustrated in the drawing will be illustrated and described.

In the embodiment illustrated in FIG. 2D, the camera module 220 may include two or more cameras 281 and 282 and at least one projector 283 capable of emitting the structured light 285. The intraoral scanner 200 according to an embodiment may emit the structured light 285 to an object 271, and the L camera 281 corresponding to the left field of view and the R camera 282 corresponding to the right field of view may obtain an L image 273 corresponding to the left field of view and an R image 275 corresponding to the right field of view, respectively. The intraoral scanner 200 may continuously obtain two-dimensional frame images including the L image 273 and the R image 275 of the object 271. For example, in a case in which the camera module 220 operates at 100 FPS, each of the L camera 281 and the R camera 282 continuously may capture 100 frame images per second. Here, the frame images obtained by the camera module 220 may be two-dimensional images corresponding to the resolution of the cameras (e.g., 281 and 282).

In addition, a plurality of frame images obtained by the two or more cameras 281 and 282 may be formatted by the camera board 230 according to another image format, for example, an HDMI format. Accordingly, an external electronic device (e.g., 120 of FIG. 1A) may receive HDMI data obtained by formatting the images obtained by the L camera 281 and the R camera 282. In addition, the external electronic device (e.g., 120 of FIG. 1A) may reconstruct a three-dimensional frame representing the surface shape of the object, from two-dimensional frames including the L image 273 and the R image 275. In detail, depth information about the object may be obtained based on the L image 273 and the R image 275 in which the structured light is imaged together. In addition, a three-dimensional image or a three-dimensional model may be reconstructed based on the depth information.

In addition, the camera board 230 or the processor 210 may generate a three-dimensional model or a three-dimensional image of the object based on the plurality of frame images obtained by the two or more cameras 281 and 282. In this case, the intraoral scanner 201 may transmit the generated three-dimensional model or three-dimensional image to the external electronic device (e.g., 120 in FIG. 1A) through a second communication network.

FIG. 2D illustrates an example in which the intraoral scanner 201 includes two cameras 281 and 282 and one projector 283. However, the embodiments are not limited to the example illustrated in FIG. 2D, and the intraoral scanner 201 may include one camera and one light emission unit. In a case in which the intraoral scanner 201 includes one camera and one projector, the projector may simultaneously perform the role of a camera obtaining an image and the role of a projector emitting structured light. In addition, according to various implementation methods of the present disclosure, a three-dimensional scanner may include a plurality of cameras and a plurality of projectors.

Meanwhile, the intraoral scanner 201 may obtain at least one image, for example, a plurality of two-dimensional frames, by scanning the object at regular time intervals (e.g., several ms to several tens of ms) while moving around the object. In addition, the intraoral scanner 201 or the external electronic device (not shown) (e.g., 120 in FIG. 1A) may obtain a plurality of three-dimensional frames from the plurality of two-dimensional frames. For example, each of at least one image sensor included in the camera module 220 included in the intraoral scanner 201 may obtain tens to hundreds of two-dimensional frames per second. In detail, tens to hundreds of three-dimensional frames may be obtained per second by using the plurality of two-dimensional frames obtained by the intraoral scanner 200. Here, each three-dimensional frame may be generated based on the plurality of two-dimensional frames. For example, one three-dimensional frame may be generated based on dozens of two-dimensional frames.

When the external electronic device (not shown) (e.g., 120 of FIG. 1A) receives image data corresponding to two-dimensional frames obtained by the intraoral scanner (e.g., 201), the external electronic device (not shown) may reconstruct a three-dimensional image or a three-dimensional model of the entire object by combining or aligning a plurality of three-dimensional frames based on the received image data.

For example, each of the L camera 281 and the R camera 282 may obtain 100 or more two-dimensional frames per second. Each of the L camera 281 and the R camera 282 may capture an image at a resolution of M*N. Here, M and N are natural numbers, M may be the number of horizontal pixels of the image to be obtained, and N may be the number of vertical pixels of the image to be obtained.

Hereinafter, for convenience of description, an example in which each of at least one image obtained by each of at least one image sensor (not shown) included in the camera 225 (e.g., the L camera 281 and the R camera 282) is a two-dimensional frame having 200 horizontal pixel values and 200 vertical pixel values (i.e., M=200, N=200) will be illustrated and described. In addition, in the above example, M and N are equal to each other, but M and N may be different natural numbers.

In addition, one pixel value may be expressed with 8 bits. In this case, each of the frame images obtained by the L camera 281 and the R camera 282 may be image data having a size or resolution of 200×200×8 bits=4000 bytes.

In addition, the camera board 230 may generate image data (specifically, HDMI data) by formatting a plurality of images obtained by the L camera 281 and the R camera 282, according to an HDMI format. Here, the HDMI data may be 2K data, 4K data, or 8K data having the HDMI format. Here, the HDMI format is in the form of an image frame having a resolution defined in the HDMI standard, and may have a format such as 1920×1080=2K resolution, 4096×2160=4K resolution, or 7680×4320=8K resolution.

Hereinafter, for convenience of description, the resolution of an image obtained by the camera (e.g., the L camera 281 and the R camera 282) included in the intraoral scanner 200 is referred to as a 'first resolution', and the resolution of image data having the HDMI format is referred to as 'second resolution'.

In addition, the first resolution may refer to the overall resolution of at least one image obtained at the same time point by the camera 225 included in the intraoral scanner (e.g., 200 or 201). For example, in a case in which the intraoral scanner (e.g., 200 or 201) includes two cameras, that is, the L camera 281 and the R camera 282, the L image 273 and the R image 275 may be obtained at the same time point. In addition, in a case in which each of the two cameras 281 and 282 has a resolution of 200 horizontal pixels and 200 vertical pixels, an image obtained by combining, in the horizontal direction, two images obtained at the same time point by the two cameras 281 and 282 may be expressed as having a resolution of 400 horizontal pixels and 200 vertical pixels. That is, when two images obtained by the two cameras 281 and 282 included in the intraoral scanner 100 or 200 are expressed as one image, the resulting image may have a resolution of 400 horizontal pixels and 200 vertical pixels. Hereinafter, for convenience of description, one image obtained by combining two images obtained at the same time point by the two cameras 281 and 282 will be referred to as a 'raw image'.

In the above example, the first resolution may be a value obtained by multiplying 200 horizontal pixels by 200 vertical pixels, or a value obtained by multiplying 400 horizontal pixels by 200 vertical pixels, and the second resolution may be 2K, 4K, 8K, or the like.

As in the above-described example, the intraoral scanner (e.g., 200 or 201) according to an embodiment of the present disclosure may generate HDMI data including pixel values of frame images obtained by each of the L camera 281 and R camera 282, and transmit the HDMI data to the external electronic device (not shown) (e.g., 120 of FIG. 1A). In detail, the intraoral scanner 200 may format the pixel values of the frame images obtained by each of the L camera 281 and the R camera 282 according to the HDMI format, such that the pixel values of the frame images obtained by each of the L camera 281 and the R camera 282 are included without change. A formatting operation according to an embodiment of the present disclosure will be described in detail below with reference to FIGS. 7 to 9.

Figure 3:
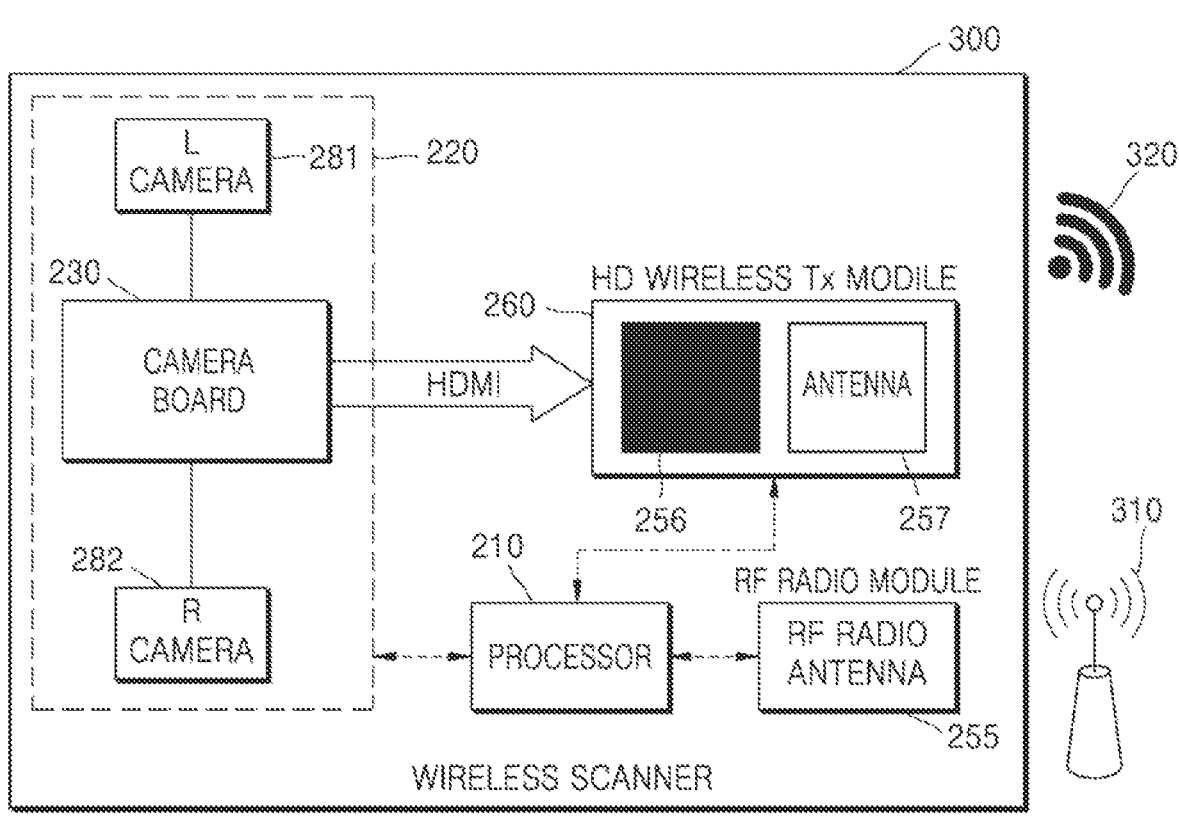
FIG. 3 is a block diagram illustrating in detail an intraoral scanner according to an embodiment of the present disclosure.

FIG. 3 is a block diagram illustrating in detail an intraoral scanner according to an embodiment of the present disclosure. An intraoral scanner 300 illustrated in FIG. 3 may correspond to the intraoral scanner 200, 201, or 202 described above with reference to FIG. 2A or 2C. Thus, in FIG. 3, the same elements as those of FIGS. 2A to 2D are illustrated by using the same reference numerals. Therefore, in describing the components illustrated in FIG. 3, redundant descriptions provided above will be omitted.

Referring to FIG. 3, the first communication module 255 may perform two-way wireless communication. In detail, the first communication module 255 may be responsible for transmission and reception of control signals through a first communication network 320. In detail, the first communication module 255 may transmit and receive a radio signal having a frequency band lower than the second frequency band, specifically, a radio-frequency (RF) signal corresponding to a control signal.

In addition, the second communication module 260 may perform one-way wireless communication. In detail, the second communication module 260 may include a transmitter 256 and an antenna 257. The transmitter 256 may generate and/or process a signal to be transmitted. In addition, the antenna 257 may output the signal generated by the transmitter 256, as a radio wave signal (or a radio signal). Alternatively, the second communication module 260 may perform two-way wireless communication.

In addition, the transmitter 256 may perform beamforming on the image data received from the camera board 230 to obtain a radio signal of the second frequency band, for example, a frequency band of 60 GHz. In addition, the antenna 257 may output the radio wave signal obtained by the transmitter 256 performing the beamforming. Here, the outputting of the radio signal by the antenna 257 may mean radiating the radio signal toward the external electronic device (not shown), which is a receiving end.

In detail, the transmitter 256 may process the radio signal to be output through the antenna 257 to have a certain phase and frequency. In detail, the transmitter 256 may perform transmit (Tx) beamforming to generate a radio signal having a certain gain, phase, and frequency. In detail, the beamforming may refer to an operation of adjusting the overall radiation direction of a beam by adjusting the phase of a signal to be radiated through the antenna 257.

The antenna 257 may output the radio wave signal generated by the transmitter 256. In detail, the antenna 257 may include an antenna array (not shown) including a plurality of antenna elements. The antenna array (not shown) may output a radio wave signal that directs a beam in a certain direction.

For example, the first communication module 255 may include an antenna that converts a control signal into a radio signal of a frequency band such as 2.4 GHz or 5 GHz and outputs the radio signal. The first communication module 255 may receive a control signal from the external electronic device (not shown) or transmit a control signal to the external electronic device (not shown).

In addition, the second communication module 260 may perform one-way wireless communication from the intraoral scanner 300 to the external electronic device (not shown) in a 60-GHz frequency band for fast transmission of image data. In this case, the transmitter 256 of the second communication module 260 may perform Tx beamforming for wireless Tx, and the antenna 257 may be a transmit antenna.

As in the above example, in a case in which the second communication module 260 is responsible for only data transmission, a transmission operation of the communication module is not delayed due to a reception operation performed by one communication module. Accordingly, the second communication module 260 may rapidly transmit image data to the external electronic device (not shown) without a delay, by performing one-way wireless communication for only transmission. In addition, the first communication module 255 may perform two-way wireless communication such that a control signal necessary for controlling the intraoral scanner 300 may be transmitted or received at any time regardless of transmission of image data. Accordingly, the transmission efficiency of the intraoral scanner may be increased, and the safety of a control operation may be improved by immediate transmission and reception of control signals.

In addition, the camera board 230 may receive a plurality of images obtained by the cameras 281 and 282, format the received images into an HDMI format, and output HDMI data. The HDMI data output from the camera board 230 may be transmitted to the second communication module 260 for transmission to an external electronic device. Subsequently, the second communication module 260 may convert the received HDMI data into a signal of a frequency band defined by a second communication network 320, and transmit the signal to the external electronic device (not shown) (e.g., 120 of FIG. 1A).

Figure 4:
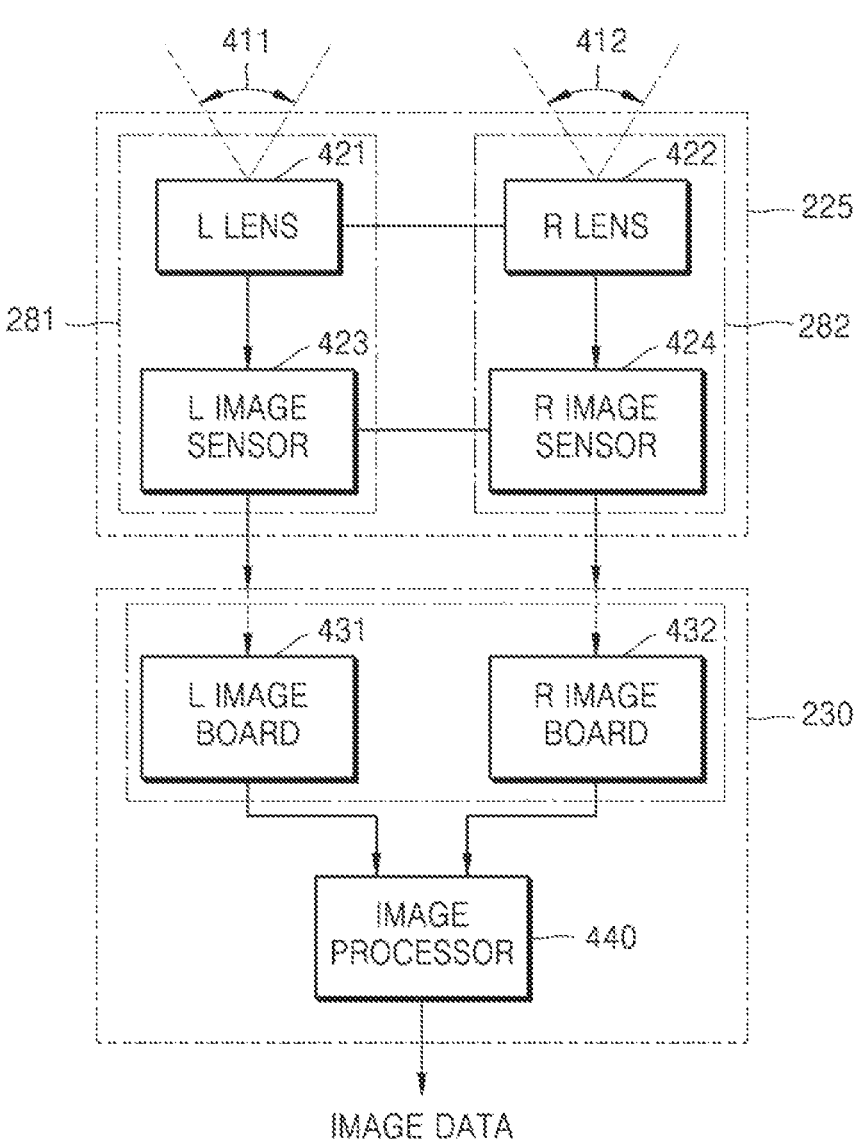
FIG. 4 is a block diagram illustrating in detail a camera device included in an intraoral scanner according to an embodiment of the present disclosure.

FIG. 4 is a block diagram illustrating in detail a camera included in an intraoral scanner according to an embodiment of the present disclosure. In FIG. 4, the same elements as those of FIGS. 2A to 2D are illustrated by using the same reference numerals. In addition, an example in which the intraoral scanner (e.g., 200, 201, 202, or 300) according to an embodiment of the present disclosure includes the L camera 281 and the R camera 282 will be illustrated and described with reference to FIG. 4.

Referring to FIG. 4, the L camera 281 may include an L lens 421 and an L image sensor 423, and the R camera 282 may include an R lens 422 and an R image sensor 424.

In addition, the camera board 230 may receive at least one image obtained by the camera 225, and format it into HDMI data.

In detail, the camera board 230 may include a memory (e.g., an L image board 431 and an R image board 432) and an image processor 440. Here, the memory may be a frame memory for storing frame images. For example, the memory may be separately formed into the L image board 431 and the R image board 432 physically or as software. As another example, the memory included in the camera board 230 may be formed as an integrated memory, and may be formed such that the internal region thereof is divided into a region corresponding to the L image board 431 and a memory region corresponding to the R image board 432. Alternatively, the memory included in the camera board 230 may be formed as two physically separated memories, which may be the L image board 431 and the R image board 432, respectively.

The L image sensor 423 may obtain an L image corresponding to an angle of view 411 (or a ROI) of the L lens 421, by receiving an electrical signal corresponding to light incident through the L lens 421. Then, the obtained L image may be transmitted to and stored in the memory of the camera board 230 (specifically, the L image board 431).

In addition, the R image sensor 424 may obtain an R image corresponding to an angle of view 412 (or a ROI) of the R lens 422, by receiving an electrical signal corresponding to light incident through the R lens 422. Then, the obtained R image may be transmitted to and stored in the memory of the camera board 230 (specifically, the R image board 432).

In addition, each of the L camera 281 and the R camera 282 may perform scanning or capturing to obtain an image having a certain resolution according to product specifications, design specifications, and/or settings. For example, in a case in which the L image sensor 423 captures an image represented by M horizontal pixels and N vertical pixels, the resolution of the L image sensor 423 may be expressed as M×N. Hereinafter, an example will be described in which M=200 and N=200 and the resolution of an image obtained by each of the L camera 281 and the R camera 282 is 200×200=400000.

In addition, each of the L camera 281 and the R camera 282 may capture tens to hundreds of images per second according to a set FPS. Here, the FPS may vary depending on product specifications, design specifications, operating environments, and/or set values of a camera included in the intraoral scanner 200.

In addition, the image processor 440 may generate image data by formatting images obtained by each of the L camera 281 and the R camera 282. For example, the image processor 440 may receive a plurality of images stored in the camera board 230, and format the plurality of received images according to an HDMI format. Accordingly, the image processor 440 may generate HDMI data having the HDMI format.

Figure 5A:
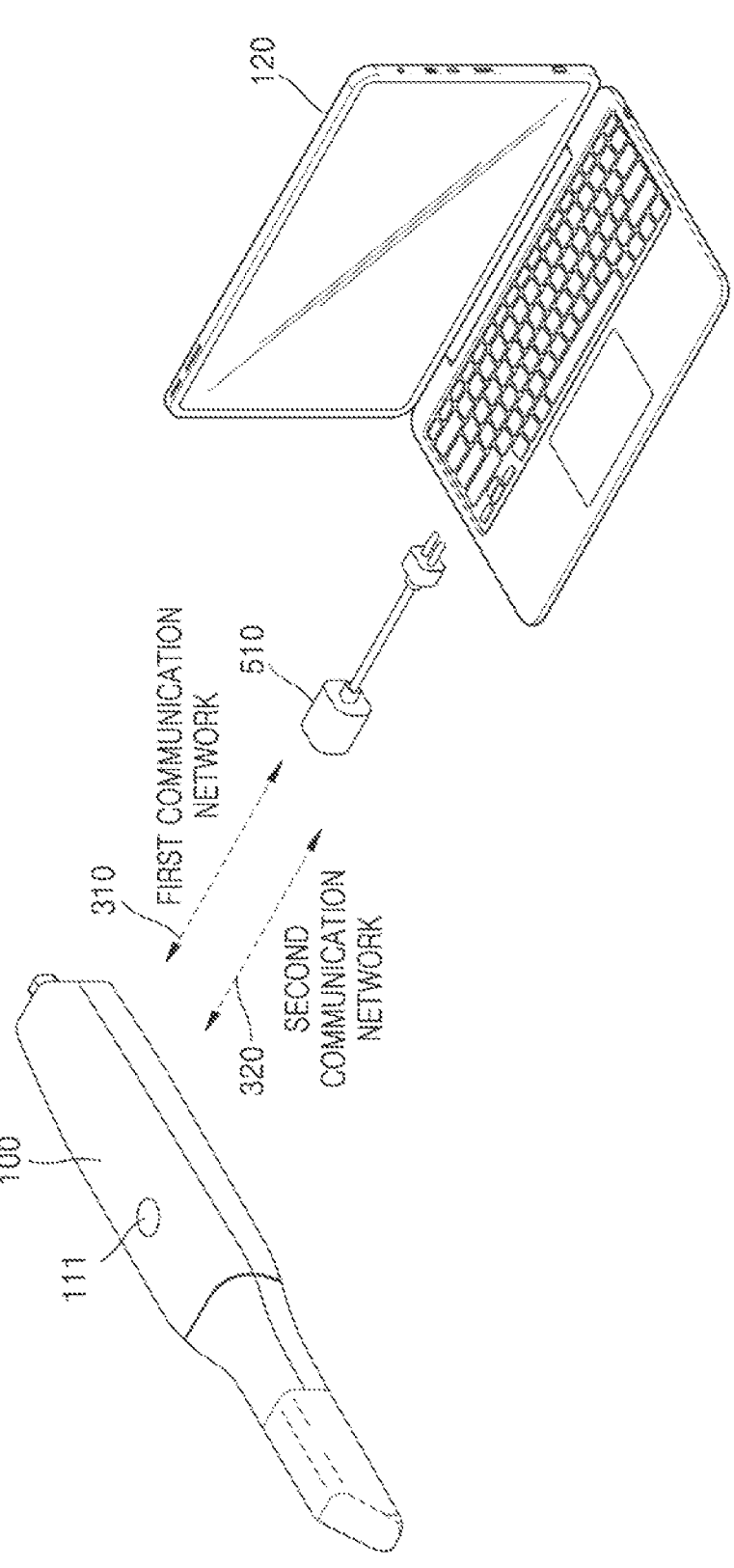
FIG. 5A is a diagram for describing communication between an intraoral scanner and an external electronic device, according to an embodiment of the present disclosure.

In the above example, each of at least one image obtained by each of one or more image sensors 423 and 424 included in the camera 225 may be a two-dimensional frame having 200 horizontal pixels and 200 vertical pixels. In addition, HDMI data that satisfies the HDMI format may be a two-dimensional frame having 1920 horizontal pixel values and 1080 vertical pixel values to have a 2K resolution. In the above example, the image processor 440 may receive an input of data of two-dimensional frames having 200 horizontal pixel values and 200 vertical pixel values, and modify the format of the input data to generate a two-dimensional frame (e.g., data having a 2K resolution defined according to the HDMI format) having 1920 horizontal pixel values and 1080 vertical pixel values. That is, data generated and output by the image processor 440 may be HDMI data that satisfies the HDMI format. FIG. 5A is a diagram for describing communication between an intraoral scanner and an external electronic device, according to an embodiment of the present disclosure. In FIG. 5A, the same elements as those of FIGS. 2A to 3 are illustrated by using the same reference numerals. Therefore, in describing the components illustrated in FIG. 5A, redundant descriptions provided above will be omitted.

Referring to FIG. 5A, a communication module 510 configured to receive a signal transmitted from the intraoral scanner 100 through at least one of a first communication network 310 and a second communication network 320 may be an internal or external component of the external electronic device 120.

For example, the communication module 510 configured to perform wireless communication with the intraoral scanner 100 may be included in the external electronic device 120.

As another example, the communication module 510 configured to perform wireless communication with the intraoral scanner 100 may be a physical device separate from the external electronic device 120. In detail, the external electronic device 120 may include the communication module 510 externally connected thereto through a connector (not shown). In a case in which the communication module 510 is a physical device separate from the external electronic device 120, and the external electronic device 120 does not support communication through the first communication network 310 and the second communication network 320, communication with the intraoral scanner 100 may be conveniently enabled by attaching the communication module 510 to the external electronic device 120.

Hereinafter, an example in which the communication module 510 is a physical device separate from the external electronic device 120 will be illustrated and described with reference to FIG. 5A and FIG. 5B. The communication module 510 will be described in detail below with reference to FIG. 5B.

Figure 5B:
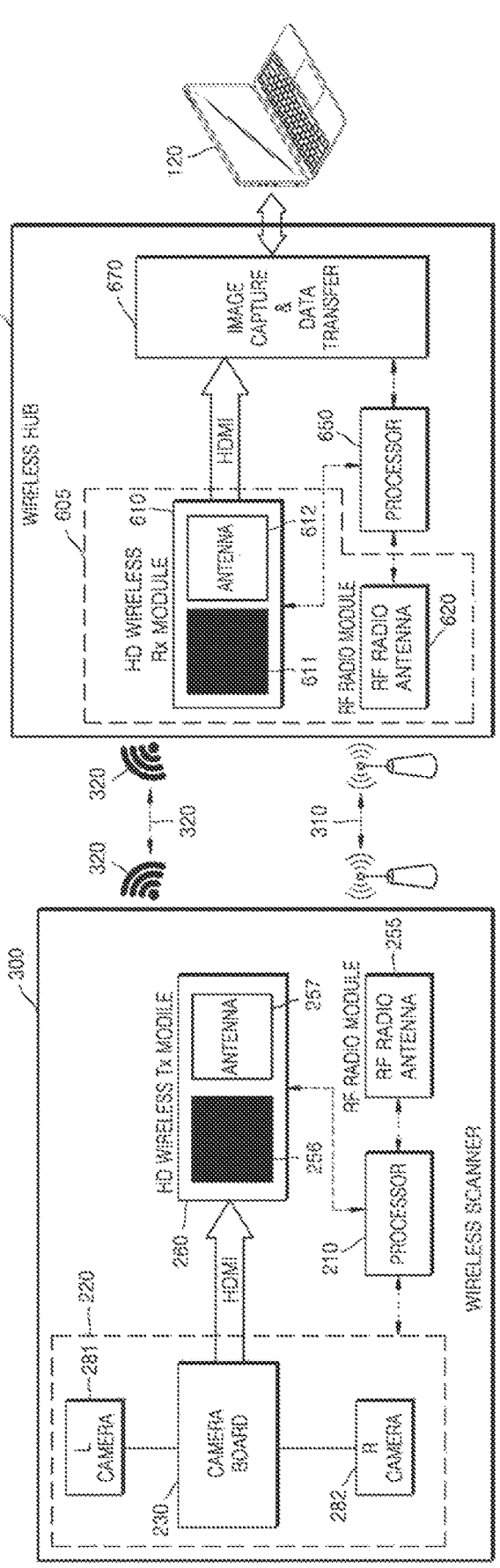
FIG. 5B is a diagram for describing in detail communication between an intraoral scanner and an external electronic device, according to an embodiment of the present disclosure.

FIG. 5B is a diagram for describing in detail communication between an intraoral scanner and an external electronic device, according to an embodiment of the present disclosure. In FIG. 5B, the same elements as those of FIGS. 1A to 5A are illustrated by using the same reference numerals. Therefore, in describing the components illustrated in FIG. 5B, redundant descriptions provided above will be omitted.

Referring to FIG. 5B, the communication module 510 responsible for communication with the intraoral scanner 300 on the side of the external electronic device 120 may include a first communication module 620, a second communication module 610, a processor 650, and a transmission interface 670.

The first communication module 620 may be responsible for communication through the first communication network 310. In detail, the first communication module 620 may perform an operation corresponding to the first communication module 255 of the intraoral scanner 300. For example, the first communication module 620 may transmit and receive a high-frequency signal of a frequency band such as 2.4 GHz or 5 GHz, to and from the first communication module 255 of the intraoral scanner 300.

The second communication module 610 may be responsible for communication through a second communication network. In detail, the second communication module 610 may perform an operation corresponding to the second communication module 260 of the intraoral scanner 300. For example, the second communication module 610 may receive a radio wave signal of a 60-GHz frequency band transmitted from the second communication module 260 of the intraoral scanner 300.

In detail, the second communication module 610 may include a receiver 611 and an antenna 612. The antenna 612 may receive a radio wave signal transmitted through the second communication network 320. In addition, the receiver 611 may generate and/or process a signal received by the antenna 612. In addition, in order to receive a radio wave signal, the receiver 611 may perform receive (Rx) beamforming to receive and process a radio wave corresponding to a certain phase and frequency. Here, a signal obtained by the RX beamforming by the receiver 611 of the second communication module 610 may be HDMI data.

The transmission interface 670 may perform an operation of transmitting a signal received from the communication module 510 to the external electronic device 120, or transmitting a signal generated by the external electronic device 120 to the first communication module 620.

In addition, when the second communication module 260 of the intraoral scanner 300 transmits image data corresponding to a plurality of images obtained by the camera module 220, the communication module 510 may receive the image data and transmit the received image data to the external electronic device 120 as it is. Alternatively, the communication module 510 may receive the image data, obtain, from the received image data, the plurality of images obtained by the camera module 220, and transmit the obtained plurality of images to the external electronic device 120. Alternatively, the communication module 510 may receive the image data, obtain, from the received image data, the plurality of images obtained by the camera module 220, process the obtained plurality of images into a three-dimensional model or a three-dimensional image, and transmit the three-dimensional model or three-dimensional image to the external electronic device 120.

In addition, when HDMI data is transmitted from the second communication module 260 of the intraoral scanner 300, the transmission interface 670 may receive the HDMI data conforming to an HDMI format and obtain a frame image from the received HDMI data. Then, the obtained image may be transmitted to the external electronic device 120. In detail, the transmission interface 670 may decode the received HDMI data to obtain a frame image before being formatted into the HDMI data by the intraoral scanner 300 (e.g., the above-described two-dimensional frame having 200 horizontal pixel values and 200 vertical pixel values). Hereinafter, a data format before being formatted into HDMI data by the intraoral scanner 300 will be referred to as 'pre-change format'.

The processor 650 may execute at least one instruction to control the overall operation of the communication module 510.

The external electronic device 120 may receive two-dimensional frames obtained by the communication module 510 performing decoding into the pre-change format. In detail, the external electronic device 120 may directly receive the two-dimensional frames obtained by the intraoral scanner 300 performing scanning, without performing a complicated decoding operation. Accordingly, the external electronic device 120 may rapidly reconstruct a three-dimensional model or a three-dimensional image necessary for oral diagnosis, based on the received two-dimensional frames.

Figure 6A:
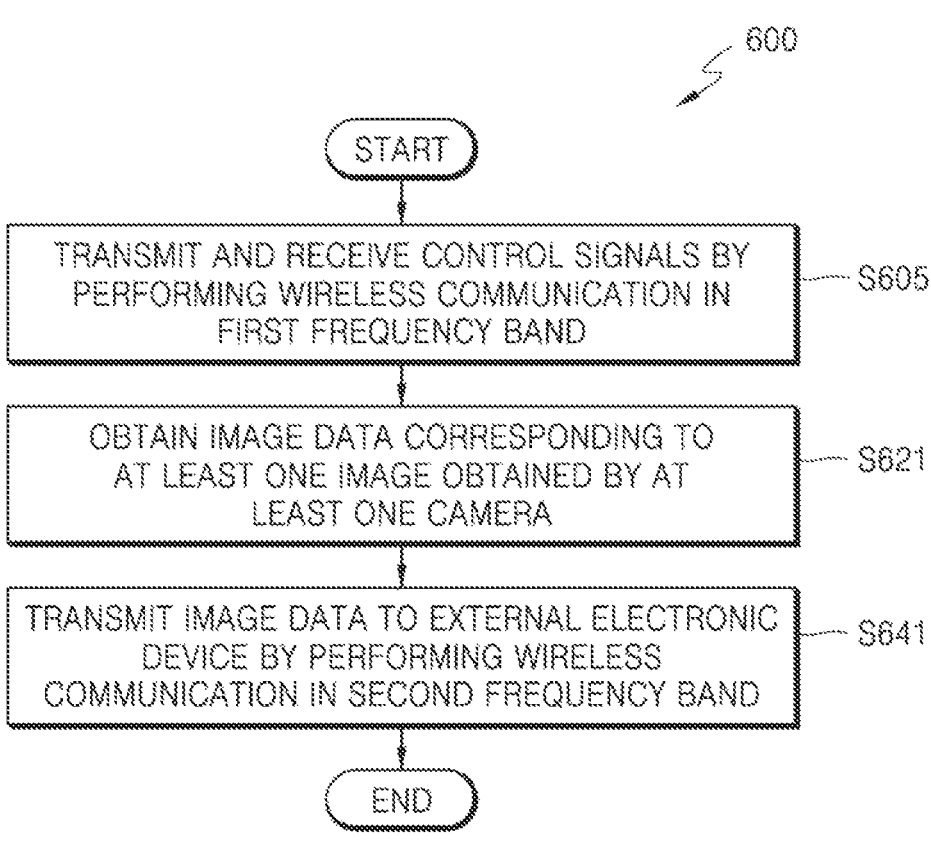
FIG. 6A is a flow chart illustrating a data transmission method of an intraoral scanner according to an embodiment of the present disclosure.

FIG. 6A is a flow chart illustrating a data transmission method of an intraoral scanner according to an embodiment of the present disclosure. In addition, FIG. 6A may be a flowchart illustrating operations performed by the intraoral scanner 100, 200, 201, 202, or 300 according to an embodiment of the present disclosure. Thus, in describing detailed operations included in a data transmission method 600 of an intraoral scanner, redundant descriptions provided above regarding the detailed operations of the intraoral scanner 100, 200, 201, 202, or 300 with reference to FIGS. 1A to 5B will be omitted.

Hereinafter, for convenience of description, an example will be described in which the data transmission method 600 of the intraoral scanner illustrated in FIG. 6A is performed by the intraoral scanner 300 described above with reference to FIG. 3.

The data transmission method 600 of the intraoral scanner according to an embodiment of the present disclosure is a method of transmitting images obtained by the intraoral scanner to an external electronic device (not shown).

Referring to FIG. 6A, the data transmission method 600 of the intraoral scanner may include transmitting and receiving control signals related to at least one of operations of obtaining and transmitting a plurality of images, by performing wireless communication with the external electronic device (not shown) (e.g., 120 of FIG. 1A) in a first frequency band (S605). Operation S605 may be performed by the first communication module 255 of the intraoral scanner 300. In detail, the first communication module 255 may transmit and receive control signals under control by the processor 210.

In addition, the data transmission method 600 of the intraoral scanner may further include obtaining image data corresponding to at least one image obtained by one or more cameras 281 and 282 included in the intraoral scanner 300 (S621). In detail, the one or more cameras 281 and 282 may scan (or photograph) an object under control by the processor 210 to capture at least one image.

Next, the data transmission method 600 of the intraoral scanner may further include transmitting the image data obtained in operation S621 to the external electronic device (not shown) by performing wireless communication in a second frequency band that is different from the first frequency band. (S641). Operation S641 may be performed by the second communication module 260 of the intraoral scanner 300. In detail, the second communication module 260 may perform a data transmission operation under control by the processor 210.

In addition, although FIG. 6A illustrates that operation S621 is performed after operation S605, the temporal order of operations S605 and S621 may be changed. That is, after the control signals according to operation S605 are transmitted and received, frame data according to operation S641 may be transmitted.

In detail, a time point at which the transmitting and receiving of the control signals (S605) are performed may vary depending on the operation state or control state of the intraoral scanner. For example, in a case in which the control signal transmitted from the external electronic device (not shown) to the intraoral scanner 300 in operation S605 is a signal for setting the camera module 220, the control signal may be transmitted before the camera module 220 performs a scanning operation. In this case, operation S605 in which the control signal is received may be performed prior to operation S621 of obtaining a plurality of images.

As another example, in a case in which the control signal transmitted from the external electronic device (not shown) to the intraoral scanner 300 in operation S605 is a control signal for controlling transmission of the image data obtained in operation S621, the control signal may be transmitted before the second communication module 260 transmits the image data. In this case, operation S605 in which the control signal is received may be performed after operation S621 of obtaining at least one image.

Figure 6B:
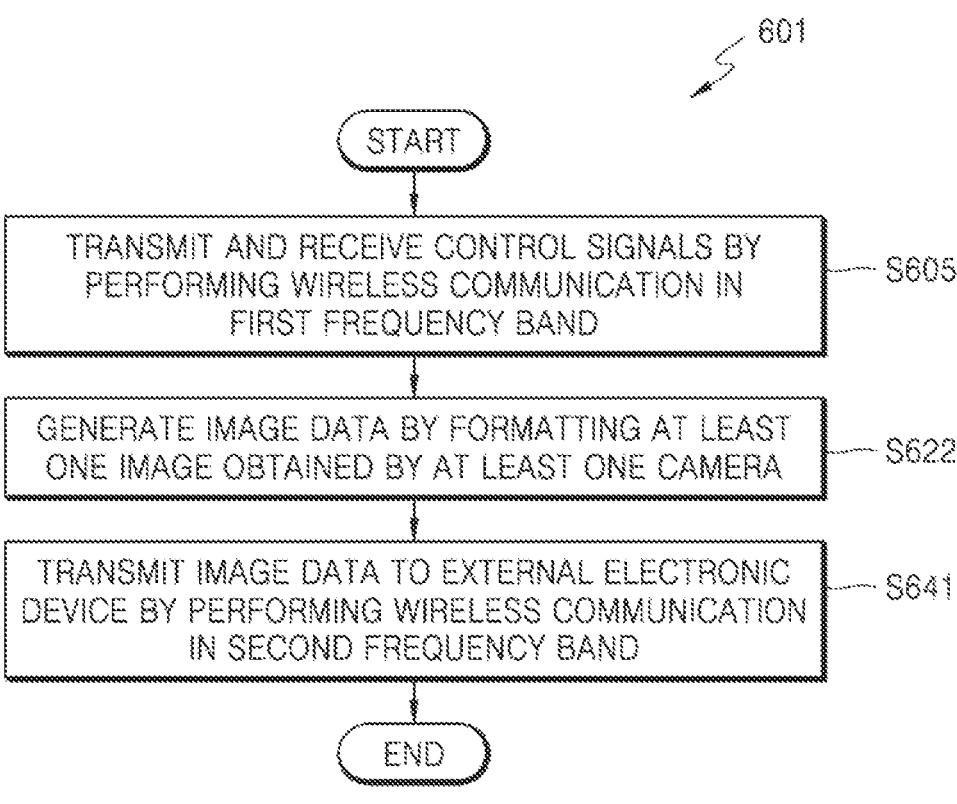
FIG. 6B is another flow chart illustrating a data transmission method of an intraoral scanner according to an embodiment of the present disclosure.

FIG. 6B is another flow chart illustrating a data transmission method of an intraoral scanner according to an embodiment of the present disclosure. In addition, FIG. 6B may be a flowchart illustrating operations performed by the intraoral scanner 100, 200, 201, 202, or 300 according to an embodiment of the present disclosure. Thus, in describing detailed operations included in a data transmission method 601 of an intraoral scanner, redundant descriptions provided above regarding the detailed operations of the intraoral scanner 100, 200, 201, 202, or 300 with reference to FIGS. 1A to 5B will be omitted. In addition, in the data transmission method 601 of the intraoral scanner, the same operations as those of FIG. 6A are illustrated by using the same reference numerals. Therefore, redundant descriptions provided above with reference to FIG. 6A will be omitted.

In addition, hereinafter, for convenience of description, an example will be described in which the data transmission method 601 of the intraoral scanner illustrated in FIG. 6B is performed by the intraoral scanner 300 described above with reference to FIG. 3.

Referring to FIG. 6B, the data transmission method 601 of the intraoral scanner may include transmitting and receiving control signals related to at least one of operations of obtaining and transmitting a plurality of images, by performing wireless communication with the external electronic device (not shown) (e.g., 120 of FIG. 1A) in a first frequency band (S605). Operation S605 may be performed by the first communication module 255 of the intraoral scanner 300. In detail, the first communication module 255 may transmit and receive control signals under control by the processor 210.

In addition, the data transmission method 601 of the intraoral scanner may further include obtaining image data by formatting at least one image obtained by one or more cameras 281 and 282 included in the intraoral scanner 300 (S621).

In detail, the one or more cameras 281 and 282 may scan (or photograph) an object under control by the processor 210 to capture at least one image. The camera board 230 may generate image data corresponding to at least one image obtained by the camera 225 by converting the format of the at least one image. Here, the converting of the format may mean modifying the format or shape of an image frame without compressing data. In detail, it may mean converting at least one image obtained by the camera 225 into an image frame having a resolution different from that of the camera 225. In detail, the camera board 230 may format at least one image obtained by the camera 225 into an image frame having a higher resolution than the resolution of the camera 225.

Next, the data transmission method 600 of the intraoral scanner may further include transmitting the image data obtained in operation S622 to the external electronic device (not shown) by performing wireless communication in a second frequency band that is different from the first frequency band. (S641). Operation S641 may be performed by the second communication module 260 of the intraoral scanner 300. In detail, the second communication module 260 may perform a data transmission operation under control by the processor 210.

In addition, although FIG. 6B illustrates that operation S622 is performed after operation S605, the temporal order of operations S605 and S622 may be changed as described above with reference to FIG. 6A. That is, after the control signals according to operation S605 are transmitted and received, frame data according to operation S641 may be transmitted.

Figure 6C:
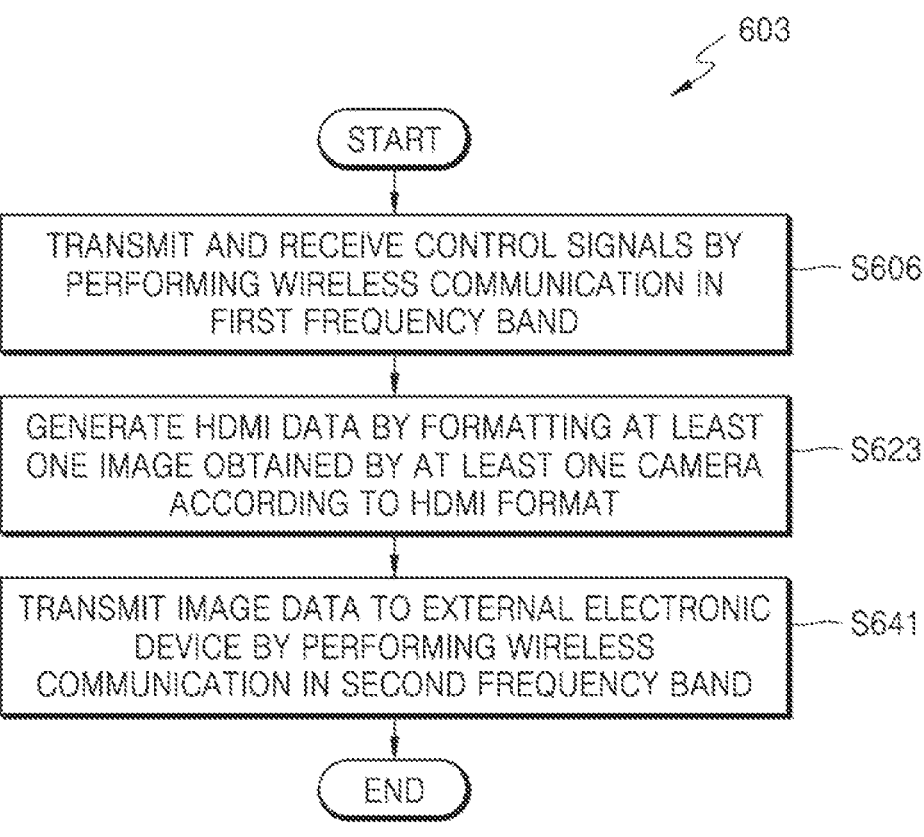
FIG. 6C is another flow chart illustrating a data transmission method of an intraoral scanner according to an embodiment of the present disclosure.

FIG. 6C is another flow chart illustrating a data transmission method of an intraoral scanner according to an embodiment of the present disclosure. In addition, FIG. 6C may be a flowchart illustrating operations performed by the intraoral scanner 100, 200, 201, 202, or 300 according to an embodiment of the present disclosure. Thus, in describing detailed operations included in a data transmission method 603 of an intraoral scanner, redundant descriptions provided above regarding the detailed operations of the intraoral scanner 100, 200, 201, 202, or 300 with reference to FIGS. 1A to 5B will be omitted. In addition, in the data transmission method 603 of the intraoral scanner, the same operations as those of FIG. 6A are illustrated by using the same reference numerals. Therefore, redundant descriptions provided above with reference to FIG. 6A will be omitted.

In addition, hereinafter, for convenience of description, an example will be described in which the data transmission method 603 of the intraoral scanner illustrated in FIG. 6C is performed by the intraoral scanner 300 described above with reference to FIG. 3.

Referring to FIG. 6C, the data transmission method 603 of the intraoral scanner may include transmitting and receiving control signals related to at least one of operations of obtaining and transmitting at least one image, by performing wireless communication with the external electronic device (not shown) (e.g., 120 of FIG. 1A) in a first frequency band (S606). Operation S606 may be performed by the first communication module 260 of the intraoral scanner 300. In detail, the first communication module 260 may transmit and receive control signals under control by the processor 210. In addition, operation S606 of FIG. 6C corresponds to operation S605 of FIG. 6A.

In addition, the data transmission method 603 of the intraoral scanner may further include obtaining HDMI data, which is image data, by formatting at least one image obtained by one or more cameras 281 and 282 included in the intraoral scanner 300 according to an HDMI format (S621).

In detail, the one or more cameras 281 and 282 may scan (or photograph) an object under control by the processor 210 to capture at least one image. The camera board 230 may format at least one image obtained by the camera 225 into a frame image corresponding to the HDMI format, and output the frame image. Here, the frame image generated by the formatting is data having the HDMI format, and thus may be referred to as 'HDMI data'.

Next, the data transmission method 603 of the intraoral scanner may further include transmitting the image data obtained in operation S622 to the external electronic device (not shown) by performing wireless communication in a second frequency band that is different from the first frequency band. (S641). Operation S641 may be performed by the second communication module 260 of the intraoral scanner 300. In detail, the second communication module 260 may perform a data transmission operation under control by the processor 210.

In addition, although FIG. 6C illustrates that operation S623 is performed after operation S606, the temporal order of operations S606 and S623 may be changed as described above with reference to FIG. 6C. That is, after the control signals are transmitted and received according to operation S606, frame data according to operation S641 may be transmitted.

For example, each of at least one image obtained by at least one image sensor (not shown) included in the camera 225 may be a two-dimensional frame having 200 horizontal pixel values and 200 vertical pixel values. In addition, the HDMI data may be a two-dimensional frame having 1920 horizontal pixel values and 1080 vertical pixel values to have a 2K resolution. In the above example, the formatting may refer to changing the data form of two-dimensional images having 200 horizontal pixel values and 200 vertical pixel values to generate a two-dimensional frame image having 1920 horizontal pixel values and 1080 vertical pixel values. An operation of formatting images obtained by the camera module 220 according to an embodiment of the present disclosure, according to an HDMI format will be described with reference to FIGS. 7 to 9. In addition, an example in which a formatting operation according to an embodiment of the present disclosure is performed by the intraoral scanner 201 illustrated in FIG. 2C will be described with reference to FIGS. 7 to 9.

Figure 7:
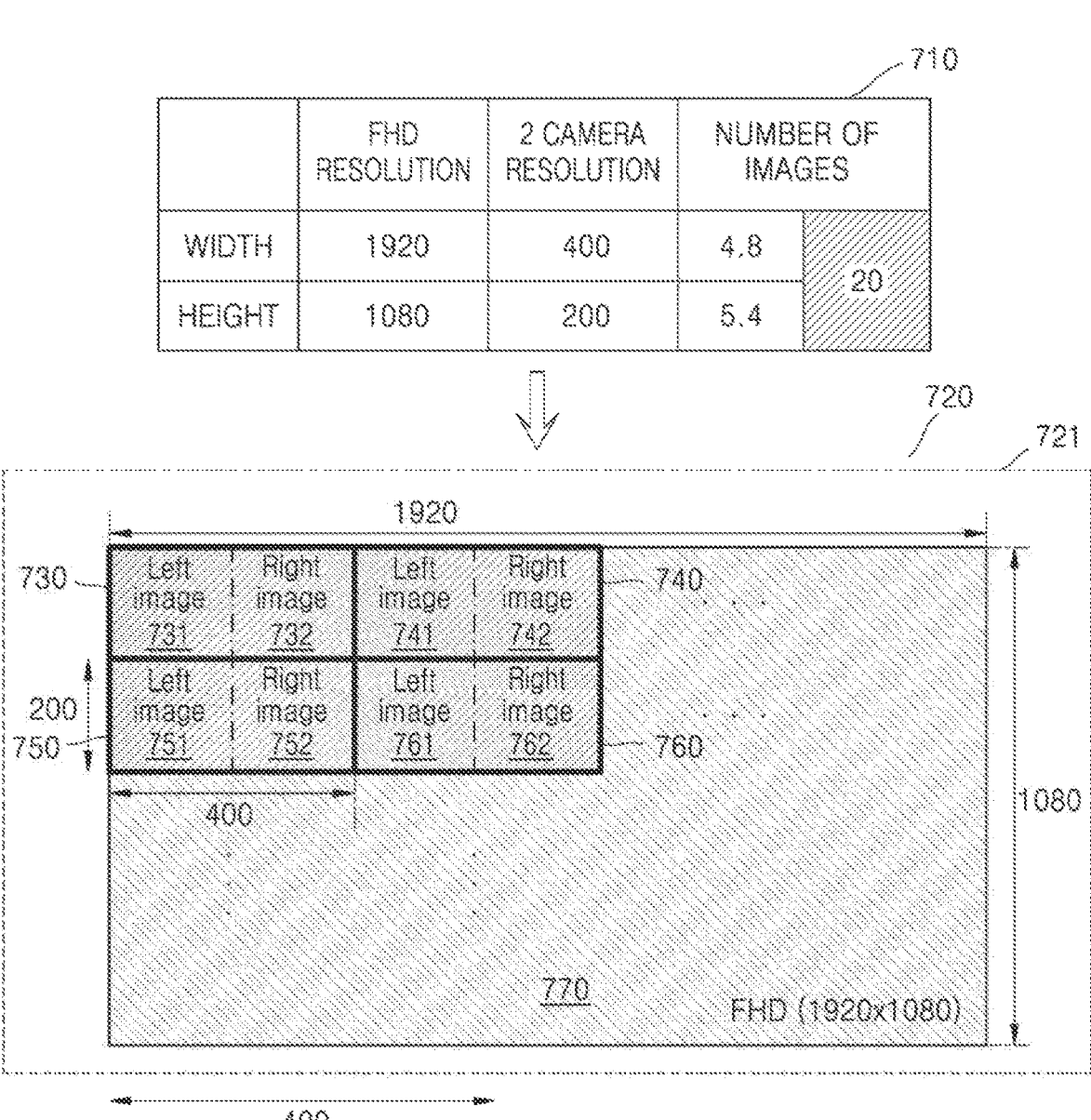
FIG. 7 is a diagram for describing an example of data transmitted from an intraoral scanner according to an embodiment of the present disclosure.

FIG. 7 is a diagram for describing an example of data transmitted from an intraoral scanner according to an embodiment of the present disclosure. In detail, FIG. 7 is a diagram illustrating image data generated by the intraoral scanner 100, 200, 201, 202, or 300 according to an embodiment of the present disclosure, that is, image data to be transmitted to an external electronic device (not shown) through the second communication module 260.

Referring to FIG. 7, a table 710 shows a full high definition (FHD) resolution, which is one of the resolutions defined in the HDMI standard, and the resolution of an image obtained by the camera included in the intraoral scanner 100, 200, 201, 202, or 300 according to an embodiment of the present disclosure.

In detail, the FHD resolution may refer to the resolution of an image having 1920 horizontal pixels and 1080 vertical pixels. Alternatively, the FHD resolution may be referred to as a 2K resolution.

In addition, in a case in which each of the two cameras 281 and 282 included in the camera module 220 has a resolution of 200 horizontal pixels and 200 vertical pixels, an image obtained by combining, in the horizontal direction, two images obtained by the two cameras 281 and 282 at once and at the same time point may be expressed as having a resolution of 400 horizontal pixels and 200 vertical pixels. That is, when two images obtained by the two cameras 281 and 282 included in the intraoral scanner 100, 200, 201, 202, or 300 are expressed as one image, the resulting image may have a resolution of 400 horizontal pixels and 200 vertical pixels. Hereinafter, for convenience of description, one image obtained by combining two images obtained by the two cameras 281 and 282 will be referred to as a 'raw image'. That is, in a case in which the camera module 220 includes two cameras 281 and 282, the resolution of the raw image may be twice the first resolution described above. In addition, in a case in which the camera module 220 includes only one camera, the resolution of the raw image may be the same as the first resolution described above.

As another example, in a case in which the intraoral scanner 100, 200, 201, 202, or 300 includes one camera, the raw image may refer to an image obtained once by the camera. That is, an image or a combination of images obtained through one scan by the intraoral scanner 100, 200, 201, 202, or 300 may be referred to as a 'raw image'.

In the example illustrated in FIG. 7, the resolution of the raw image may be expressed as a value obtained by multiplying 400 vertical pixels by 200 horizontal pixels, and the resolution (specifically, the second resolution) of a frame image (e.g., 720) having the HDMI format is 2K.

The camera module 220 may continuously perform image capture according to a set FPS. In detail, a first L image 731 and a first R image 732 may be obtained at a first time point, a second L image 741 and a second R image 742 may be obtained at a second time point subsequent to the first time point, a third L image 751 and a third R image 752 may be obtained at a third time point subsequent to the second time point, and a fourth L image 761 and a fourth R image 762 may be obtained at a fourth time point subsequent to the third time point.

For example, the processor 210 may receive a control signal for requesting image scanning, from the external electronic device (not shown) through the first communication module 255. The operation of receiving a control signal may correspond to operations S605 and S606 described above with reference to FIGS. 6A to 6C. Then, in response to the received control signal, the processor 210 may transmit, to the projector 283, a signal for requesting to stand by for the image scanning. When receiving the signal for requesting to stand by for the image scanning, the projector 283 may output, to the camera 225, a trigger signal for synchronizing light output with the image scanning. In addition, the projector 283 may output light to an object in response to the output of the trigger signal, and the camera 225 may perform an image capture operation in response to receiving the trigger signal. Accordingly, the projector 283 and the camera 225 may output light and perform the image capture operation, respectively, in synchronization with each other.

In addition, for example, the processor 210 may receive a control signal for requesting image scanning, from the external electronic device (not shown) through the first communication module 255. Here, the image scanning may be performed based on a confocal method. In addition, the operation of receiving a control signal may correspond to operations S605 and S606 described above with reference to FIGS. 6A to 6C. Then, in response to the received control signal, the processor 210 may transmit, to a light emission unit (not shown), a signal for requesting to stand by for the image scanning. When receiving the signal for requesting to stand by for the image scanning, the light emission unit (not shown) may drive a lens included in the camera to adjust the focal point. Then, the lens may be moved to a certain position. Next, the processor 210 may output, to the camera 225, a control signal (e.g., a trigger signal) for synchronizing driving of the lens with the image scanning. Accordingly, the driving of the lens included in the camera 225 and the capturing by the image sensor may be performed in synchronization with each other.

In an embodiment of the present disclosure, the camera board 230 may generate a frame image 720 having the second resolution (specifically, a 2K resolution), by combining a plurality of images (e.g., 731, 732, 741, 742, 751, 752, 761, and 762) having the first resolution with each other without change. In addition, in the frame image 720, a region 770 that is not filled with the plurality of images (e.g., 731, 732, 741, 742, 751, 752, 761, and 762) having the first resolution may be processed to be a null data region. Alternatively, the region 770 that is not filled with the plurality of images (e.g., 731, 732, 741, 742, 751, 752, 761, and 762) having the first resolution may be filled with data with an offset value.

In the example of FIG. 7, the camera board 230 may format the plurality of images (e.g., 731, 732, 741, 742, 751, 752, 761 and 762) obtained by the two cameras 281 and 282 into the frame image 720, which is one piece of HDMI data, according to an HDMI format, and then output the frame image 720.

In detail, the camera board 230 of the intraoral scanner 300 may receive a plurality of images obtained in real time by the two cameras 281 and 282. In detail, the camera board 230 may receive a plurality of raw images 730, 740, 750, and 760 obtained in real time by the two cameras 281 and 282. In addition, each of the plurality of raw images 730, 740, 750, and 760 may be an image including color information about an object or an image representing depth information (e.g., three-dimensional information) about the object. In addition, the image including the color information about the object may include information about at least one color among red (R), green (G), and blue (B). Alternatively, the image including the color information about the object may include information about at least one color among white (W), red (R), green (G), and blue (B).

In addition, the camera board 230 may format the received raw image into an HDMI format having an FHD resolution to generate the frame image 720 that is HDMI data, as illustrated in block 721.

The FPS defined in the HDMI standard may have a value of 30, 60, or 120. Accordingly, the frame image 720 generated by the camera board 230 may be transmitted to the external electronic device (not shown) according to the FPS defined in the HDMI standard.

For example, when the FPS according to the HDMI standard is 60, the second communication module 260 of the intraoral scanner 100, 200, or 300 according to an embodiment of the present disclosure may transmit the frame image 720 to the external electronic device (not shown) at a rate of 60 images per second.

In the example illustrated in FIG. 7, one frame image 720, which is HDMI data having a resolution of 2K, may include 20 raw images (e.g., 730) as illustrated in the table 710.

For example, assume that the external electronic device (not shown) needs a raw images (e.g., 730) to generate one three-dimensional intraoral image. Hereinafter, an example of a=10 will be described. In this case, one frame image 720 may be transmitted to the external electronic device (not shown), and the external electronic device (not shown) may reconstruct one three-dimensional intraoral image immediately upon receiving the one frame image 720. In the example illustrated in FIG. 7, HDMI data may be generated by including 10 raw images necessary for reconstructing one three-dimensional intraoral image in the frame image 720 and processing the remaining data region to be null. In this case, one frame image 720 may be transmitted to the external electronic device (not shown), and the external electronic device (not shown) may reconstruct two three-dimensional intraoral images immediately upon receiving the one frame image 720.

According to the above-described embodiment, image data necessary to restore a three-dimensional intraoral image may be received faster than when receiving 10 raw images (e.g., 730) that are continuously transmitted. In addition, in a case in which the FPS according to the HDMI standard is 60, the external electronic device (not shown) may receive the frame image 720 in a rate of 60 images per second, and thus may reconstruct 60 three-dimensional intraoral images per second.

In addition, in the example of FIG. 7, the frame image 720 may include up to 20 raw images, and thus, HDMI data may be generated such that the frame image 720 includes 20 raw images.

As described above, according to an embodiment of the present disclosure, it is possible to rapidly transmit a large amount of data including a plurality of raw images to the external electronic device (not shown), while transmitting the frame image 720 to the external electronic device (not shown) at an FPS lower than the FPS of the two cameras 281 and 282 included in the intraoral scanner.

In an embodiment of the present disclosure, at least one camera included in the intraoral scanner 100, 200, 201, 202, or 300 may perform image capture at a first FPS. Then, when the second communication module 260 generates a frame image that is HDMI data and transmits the frame image to the external electronic device (not shown), the frame image may be transmitted at a second FPS defined in the HDMI standard and having a value less than the first FPS.

Figure 8:
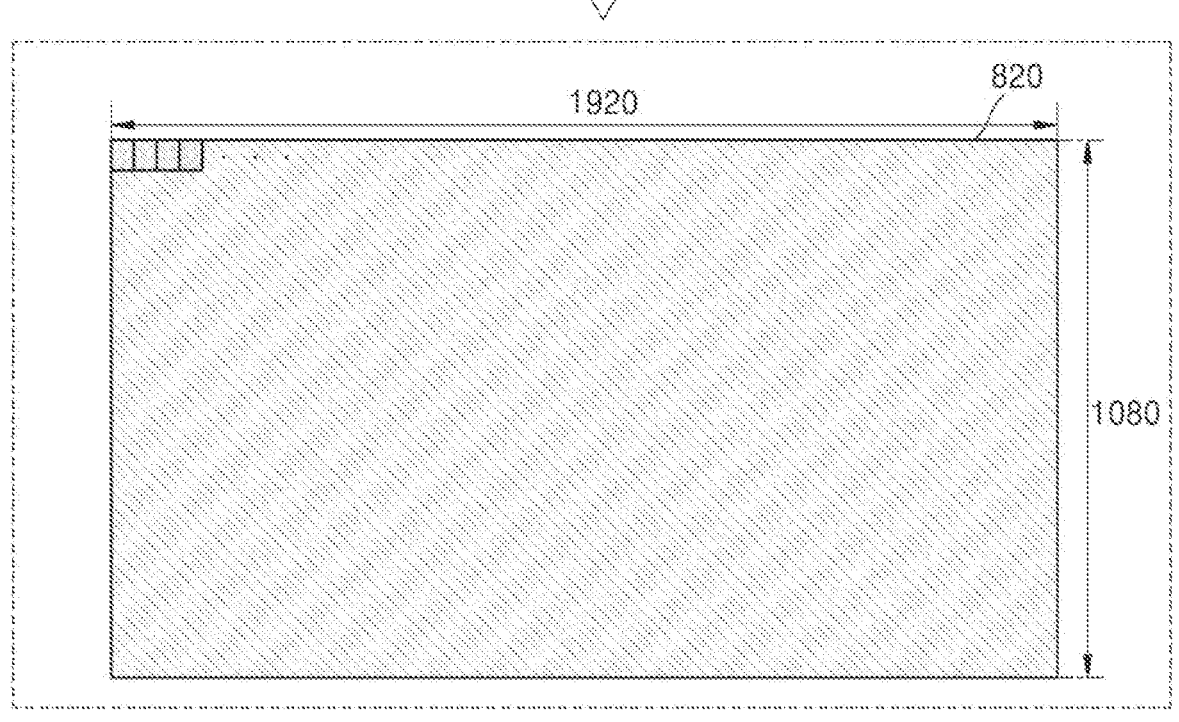
FIG. 8 is a diagram for describing another example of data transmitted from an intraoral scanner according to an embodiment of the present disclosure.

FIG. 8 is a diagram for describing another example of data transmitted from an intraoral scanner according to an embodiment of the present disclosure.

Referring to FIG. 8, a table 810 shows an FHD resolution, which is one of the resolutions defined in the HDMI standard, and the number of pixels corresponding to the resolution of an image obtained by the camera included in the intraoral scanner 100, 200, 201, 202, or 300 according to an embodiment of the present disclosure. A frame image 820 illustrated in FIG. 8 may correspond to the frame image 720 described above with reference to FIG. 7.

In detail, the FHD resolution may refer to the resolution of an image having 1920 horizontal pixels and 1080 vertical pixels, and thus, the total number of pixels corresponding to the FHD resolution is 1920×1080=2073600. In addition, the number of pixels of a raw image (e.g., 730) is 400×200=80000. Therefore, in a case in which one frame image 820 having the FHD resolution is filled with pixel values of a plurality of raw images (e.g., 730, 740, 750, and 760), the frame image 820 may include pixel values of 2073600/ 80000=(approximately) 25.92 raw images (e.g., 730, 740, 750, and 760).

Accordingly, in the example illustrated in FIG. 8, the camera board 230 may receive 25.92 raw images, format them according to the HDMI format, and generate one frame image 820 having the HDMI format.

For example, in a case of filling one frame image 820 with pixel values of a plurality of raw images (e.g., 730, 740, 750, and 760 of FIG. 7), the pixel values included in the raw image (e.g., 730) may be arranged in the frame image 820 in the order of rows or columns. Then, the external electronic device (not shown) may read the pixel values included in the frame image 820 in the order of rows or columns to obtain a plurality of raw images (e.g., 730, 740, 750, and 760).

As described above, assume that the external electronic device (not shown) needs 10 raw images (e.g., 730) to generate one three-dimensional intraoral image. In this case, when the intraoral scanner 100, 200, 201, 202, or 300 according to an embodiment of the present disclosure transmits, to the external electronic device (not shown), one frame image 820 formatted according to the HDMI format, the external electronic device (not shown) may reconstruct two three-dimensional intraoral images immediately upon receiving the frame image 820.

Figure 9:
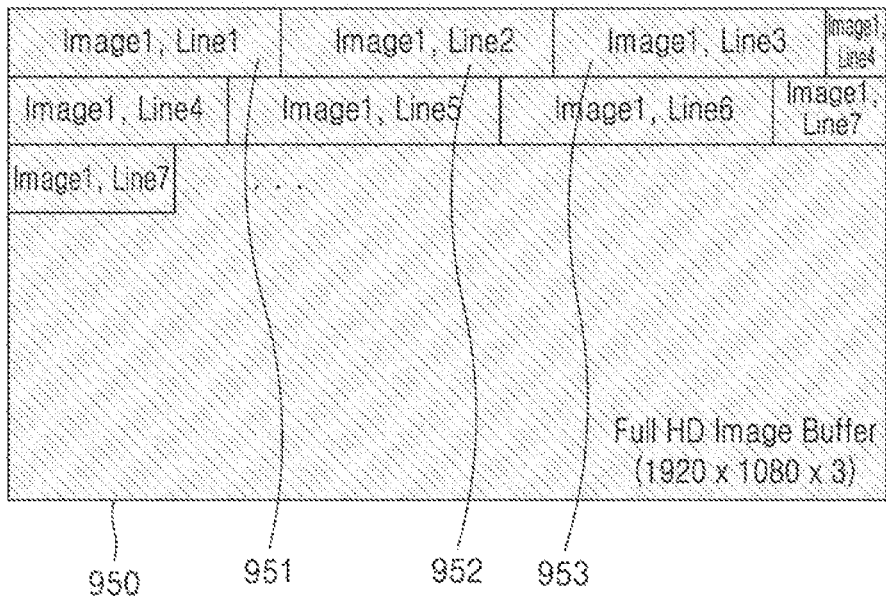
FIG. 9 is a diagram for describing another example of data transmitted from an intraoral scanner according to an embodiment of the present disclosure.

FIG. 9 is a diagram for describing another example of data transmitted from an intraoral scanner according to an embodiment of the present disclosure. A frame image 950 illustrated in FIG. 9 may correspond to the frame image 720 described above with reference to FIG. 7.

The frame image 950 may be generated by continuously arranging lines of a plurality of continuously obtained raw images (e.g., 730, 740, 750, and 760). In detail, assuming that a horizontal row of pixels of the raw image is a line, the frame image 950 may be generated by arranging, in the horizontal direction, a first line 951, a second line 952, a third line 953, and the like of the raw image.

In detail, as described above with reference to FIG. 7, in a case in which the raw image (e.g., 730) is an image having a resolution of 400×200, the first line 951 that is at the top of the raw image 730 and is a horizontal row may include 400 pixel values. In addition, the second line 953 below the first line of the raw image 730 may also include 400 pixel values. Accordingly, when the plurality of raw images (e.g., 730, 740, 750, and 760) are arranged in one frame image 950 as in the above example, approximately 25 raw images may be included in one frame image 950.

Figure 10A:
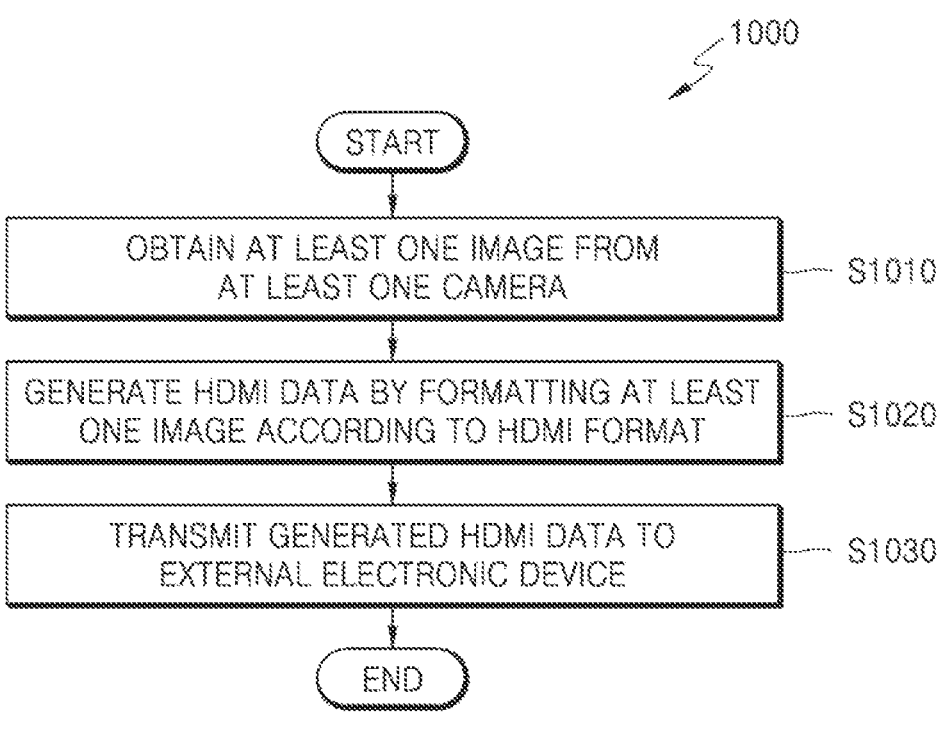
FIG. 10A is a flow chart illustrating a data transmission method of an intraoral scanner according to an embodiment of the present disclosure.

FIG. 10A is a flow chart illustrating a data transmission method of an intraoral scanner according to an embodiment of the present disclosure. In addition, FIG. 10A may be a flowchart illustrating operations performed by the intraoral scanner 100, 200, 201, 202, or 300 according to an embodiment of the present disclosure. Thus, in describing detailed operations included in a data transmission method 1000 of an intraoral scanner, redundant descriptions provided above regarding the detailed operations of the intraoral scanner 100, 200, 201, 202, or 300 with reference to FIGS. 1A to 9 will be omitted.

Hereinafter, for convenience of description, an example will be described in which the data transmission method 1000 of the intraoral scanner illustrated in FIG. 10A is performed by the intraoral scanner 200 described above with reference to FIG. 2A.

The data transmission method 1000 of the intraoral scanner according to an embodiment of the present disclosure is a method of transmitting images obtained by the intraoral scanner to an external electronic device (not shown).

Referring to FIG. 10A, the data transmission method 600 of the intraoral scanner may include obtaining at least one image from at least one camera 225 included in the intraoral scanner 200 (S1010). In detail, the at least one camera 225 may scan (or photograph) an object under control by the processor 210 to capture at least one image.

Next, the data transmission method 1000 of the intraoral scanner may further include obtaining HDMI data, which is image data, by formatting the at least one image obtained by the at least one camera 225 included in the intraoral scanner 200 according to an HDMI format (S1020). In detail, the at least one camera 225 may scan (or photograph) the object under control by the processor 210 to capture at least one image. The camera board 230 may format a plurality of images obtained by the camera 225 into frame images corresponding to the HDMI format, and output the frame images. Here, the frame image generated by the formatting is data having the HDMI format, and thus may be referred to as 'HDMI data'. The formatting operation is described in detail above with reference to FIGS. 7 to 9, and thus, redundant descriptions will be omitted.

Next, the data transmission method 1000 of the intraoral scanner may further include transmitting the HDMI data generated in operation S1020 to the external electronic device (not shown) (S1030). In detail, the communication unit 250 may perform a data transmission operation under control by the processor 210.

Figure 10B:
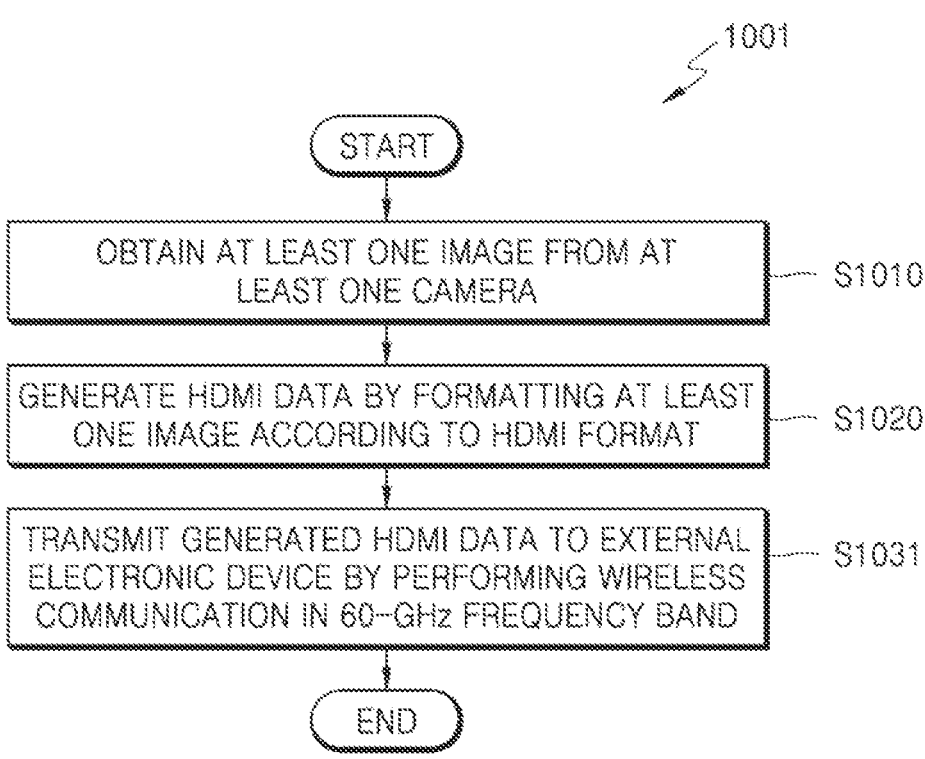
FIG. 10B is another flow chart illustrating a data transmission method of an intraoral scanner according to an embodiment of the present disclosure.

FIG. 10B is another flow chart illustrating a data transmission method of an intraoral scanner according to an embodiment of the present disclosure. In addition, FIG. may be a flowchart illustrating operations performed by the intraoral scanner 100, 200, 201, 202, or 300 according to an embodiment of the present disclosure. Thus, in describing detailed operations included in a data transmission method 1001 of an intraoral scanner, redundant descriptions provided above regarding the detailed operations of the intraoral scanner 100, 200, 201, 202, or 300 with reference to FIGS. 1A to 9 will be omitted. In addition, in FIG. 10B, the same operations as those of FIG. 10A are illustrated by using the same reference numerals.

Hereinafter, for convenience of description, an example will be described in which the data transmission method 1001 of the intraoral scanner illustrated in FIG. 10B is performed by the intraoral scanner 200 described above with reference to FIG. 2A.

Referring to FIG. 10B, the data transmission method 1001 of the intraoral scanner may include transmitting the HDMI data generated in operation S1020 to the external electronic device (not shown) by performing wireless communication in a 60-GHz frequency band (S1031). In detail, the communication unit 250 may perform a data transmission operation under control by the processor 210.

In detail, the communication unit 250 of the intraoral scanner 200 according to an embodiment of the present disclosure may include a communication module (e.g., the second communication module 260 of FIG. 2C) capable of performing wireless communication at 60 GHz. In this case, the communication unit 250 including the communication module capable of performing wireless communication at 60 GHz (e.g., the second communication module 260 of FIG. 2C) may transmit the HDMI data generated in operation S1020 to the external electronic device (not shown) by performing wireless communication in a 60-GHz frequency band, under control by the processor 210 (S1031).

FIG. 10C is another flow chart illustrating a data transmission method of an intraoral scanner according to an embodiment of the present disclosure. In addition, FIG. may be a flowchart illustrating operations performed by the intraoral scanner 100, 200, 201, 202, or 300 according to an embodiment of the present disclosure. Thus, in describing detailed operations included in a data transmission method 1002 of an intraoral scanner, redundant descriptions provided above regarding the detailed operations of the intraoral scanner 100, 200, 201, 202, or 300 with reference to FIGS. 1A to 9 will be omitted. In addition, in FIG. 10C, the same operations as those of FIG. 10A are illustrated by using the same reference numerals.

Hereinafter, for convenience of description, an example will be described in which the data transmission method 1002 of the intraoral scanner illustrated in FIG. 10A is performed by the intraoral scanner 300 described above with reference to FIG. 3.

Referring to FIG. 10C, the data transmission method 1002 of the intraoral scanner may include transmitting and receiving control signals related to at least one of operations of obtaining and transmitting a plurality of images, by performing wireless communication with the external electronic device (not shown) (e.g., 120 of FIG. 1A) in a first frequency band (S1005). Here, operation S1005 may be performed by the first communication module 255 of the intraoral scanner 300. In detail, the first communication module 255 may transmit and receive control signals under control by the processor 210. In addition, operation S1005 corresponds to operation S606 described above with reference to FIG. 6C, and thus, redundant descriptions will be omitted.

In addition, the data transmission method 1002 of the intraoral scanner may further include obtaining at least one image from at least one camera 225 included in the intraoral scanner 600 (S1010). In detail, the at least one camera 225 may scan (or photograph) an object under control by the processor 210 to capture at least one image.

In addition, although FIG. 10C illustrates that operation S1010 is performed after operation S1005, the temporal order of operations S1005 and S1010 may be changed as described above with reference to FIG. 6C. That is, after the at least one image according to operation S1010 is obtained, the control signals according to operation S1005 may be transmitted and received.

Next, the data transmission method 1002 of the intraoral scanner may further include obtaining HDMI data, which is image data, by formatting the at least one image obtained by the at least one camera 225 included in the intraoral scanner 200 according to an HDMI format (S1020).

Next, the data transmission method 1002 of the intraoral scanner may further include transmitting the HDMI data obtained in operation S1020 to the external electronic device (not shown) by performing wireless communication in a second frequency band that is different from the first frequency band. (S1032). Operation S1032 may be performed by the second communication module 260 of the intraoral scanner 300. In detail, the second communication module 260 may perform a data transmission operation under control by the processor 210. In detail, the second communication module 260 may transmit the HDMI data formatted according to the HDMI standard, to the external electronic device (not shown) in a 60-GHz band.

As described above with reference to FIGS. 10A to 10C, according to the disclosed embodiments, a large amount of data may be rapidly transmitted to the external electronic device (not shown) without omission or loss, by transmitting, to the external electronic device (not shown), HDMI data including image data obtained by the camera 225 of the intraoral scanner 100, 200, 201, 202, or 300, through the second frequency band, for example, a 60-GHz band. In addition, by transmitting and receiving, through the first frequency band lower than the second frequency band, control signals related to obtaining and transmitting images by the intraoral scanner 200, the reliability of signal transmission and reception may be improved to safely transmit and receive the control signals to and from the external electronic device (not shown). In detail, as the frequency band decreases, signal transmission stability may increase. Thus, when an error occurs in transmitting a large amount of image data in the second frequency band, in the disclosed embodiments, the control signals are transmitted to and received from the external electronic device (not shown) in the first frequency band lower than the second frequency band, such that a user may quickly recognize and deal with the error in the transmission of the large amount of image data.

In addition, the intraoral scanner may transmit and receive required control signals without a delay and an interruption to the transmission of the image data, by transmitting the HDMI data including image data, and the control signals through different communication networks (or different communication channels).

In addition, because HDMI is a protocol optimized for transmission of image data, images may be rapidly transmitted and received when HDMI data is received. In an embodiment of the present disclosure, HDMI data obtained by conversion into an HDMI format that satisfies the HDMI communication standard is transmitted as it is. Accordingly, the external electronic device (not shown) receiving the HDMI data from the intraoral scanner may rapidly obtain and process the images.

In addition, because the control signals are transmitted and received separately from the image data, there is no need to modify the existing HDMI format in order to transmit the control signals together with the image data, and a general HDMI communication module may be applied to the disclosed second communication module as it is, and used. Therefore, there is no need to modify an existing HDMI communication module or develop an HDMI communication module to transmit and receive control signals. Therefore, cost expenditures and a delay for modification and development may be minimized.

In addition, the data transmission method of the intraoral scanner according to an embodiment of the present disclosure may be embodied as program instructions executable by various computer devices, and recorded on a computer-readable medium. In addition, an embodiment of the present disclosure may be implemented in a computer-readable recording medium having recorded thereon one or more programs including instructions for executing the data transmission method of the intraoral scanner.

The computer-readable medium may include program instructions, data files, data structures, or the like separately or in combinations. The program instructions to be recorded on the medium may be specially designed and configured for the present disclosure or may be well-known to and be usable by those skill in the art of computer software. Examples of the computer-readable recording medium include magnetic media such as hard disks, floppy disks, or magnetic tapes, optical media such as compact disc ROMs (CD-ROMs) or digital video discs (DVDs), magneto-optical media such as floptical disks, and hardware devices such as ROM, RAM, and flash memory, which are specially configured to store and execute program instructions. Examples of the program instructions include not only machine code, such as code made by a compiler, but also high-level language code that is executable by a computer by using an interpreter or the like.

Here, the machine-readable storage medium may be provided in the form of a non-transitory storage medium. Here, the term 'non-transitory' merely means that the storage medium does not refer to a transitory electrical signal but is tangible, and does not distinguish whether data is stored semi-permanently or temporarily on the storage medium. For example, the non-transitory storage medium may include a buffer in which data is temporarily stored.

According to an embodiment, the data transmission method of the intraoral scanner according to various embodiments disclosed herein may be included in a computer program product and then provided. The computer program products may be traded as commodities between sellers and buyers. The computer program product may be distributed in the form of a machine-readable storage medium (e.g., a CD-ROM), or may be distributed online (e.g., downloaded or uploaded) through an application store (e.g., Play Store™) or directly between two user devices (e.g., smart phones). In a case of online distribution, at least a portion of the computer program product (e.g., a downloadable app) may be temporarily stored in a machine-readable storage medium such as a manufacturer's server, an application store's server, or a memory of a relay server.

In detail, the data transmission method of the intraoral scanner according to an embodiment of the present disclosure may be implemented as a computer program product including a recording medium having recorded thereon a program for obtaining a multilingual sentence, obtaining vector values respectively corresponding to words included in the multilingual sentence by using a multilingual translation model, converting the obtained vector values into target vector values corresponding to a target language, and obtaining a sentence in the target language based on the converted target vector values.

Although embodiments have been described above in detail, the scope of the present disclosure is not limited thereto, and various modifications and alterations by those skill in the art using the basic concept of the present disclosure defined in the following claims also fall within the scope of the present disclosure.

The invention claimed is:

1. An intraoral scanner for dental treatment, the intraoral scanner comprising:
   a light emission unit configured to output light to be projected onto an object;
   a camera module comprising at least one camera configured to obtain at least one intraoral image based an image formed by the light reflected from the object;
   a communication unit comprising a first communication module configured to perform wireless communication in a first frequency band, and a second communication module configured to perform wireless communication in a second frequency band with an external electronic device which processes intraoral image data corresponding to the at least one intraoral image; and
   a processor configured to execute at least one instruction to:
      perform control such that control signals related to at least one of an operation of obtaining the at least one intraoral image and an operation of transmitting the at least one intraoral image are transmitted to and received from the external electronic device, through the first communication module performing the wireless communication in the first frequency band, and
      perform control such that the at least one intraoral image is transmitted to the external electronic device through the second communication module performing the wireless communication in the second frequency band.

2. The intraoral scanner of claim 1, wherein the camera module comprises a camera board configured to obtain the intraoral image data corresponding to the at least one intraoral image, by processing the at least one intraoral image.

3. The intraoral scanner of claim 1, wherein the processor is further configured to execute the at least one instruction to obtain the intraoral image data corresponding to the at least one intraoral image obtained by the at least one camera, by processing the at least one intraoral image, perform control such that the control signals related to the at least one of the operations of obtaining and transmitting the at least one intraoral image are transmitted to and received from the external electronic device through the first communication module performing the wireless communication in the first frequency band, and perform control such that the at least one intraoral image is transmitted to the external electronic device through the second communication module performing the wireless communication in the second frequency band.

4. The intraoral scanner of claim 3, wherein the second communication module is further configured to perform the wireless communication in the second frequency band that is a frequency band different from the first frequency band.

5. The intraoral scanner of claim 3, wherein the processor is further configured to execute the at least one instruction to receive the control signal regarding a setting of the at least one camera from the external electronic device through the first communication module, and control the at least one camera to obtain the at least one intraoral image based on the control signal.

6. The intraoral scanner of claim 3, further comprising a light emission unit configured to output light to be projected onto an object,
   wherein the processor is further configured to execute the at least one instruction to, based on the control signal for requesting image scanning being received from the external electronic device through the first communication module, perform control such that a trigger signal for synchronizing the outputting of the light with the image scanning is output from the light emission unit to the at least one camera.

7. The intraoral scanner of claim 3, further comprising a light emission unit configured to output light to be projected onto an object,
   wherein the processor is further configured to execute the at least one instruction to, based on the control signal for controlling at least one of an output timing and an output intensity of the light being received from the external electronic device through the first communication module, control the light emission unit based on the control signal.

8. The intraoral scanner of claim 3, further comprising a light emission unit configured to output light toward an object,
   wherein the at least one camera is further configured to obtain the at least one intraoral image based on driving of a lens, and the processor is further configured to execute the at least one instruction to, based on the control signal for requesting image scanning being received from the external electronic device through the first communication module, perform control such that a trigger signal for synchronizing the driving of the lens with the image scanning is output to the at least one camera.

9. The intraoral scanner of claim 3, wherein the second frequency band is a frequency band higher than the first frequency band.

10. The intraoral scanner of claim 3, wherein the first communication module is further configured to perform two-way wireless communication between the scanner and the external electronic device in the first frequency band, and the second communication module is further configured to perform one-way wireless communication from the scanner to the external electronic device in the second frequency band.

11. The intraoral scanner of claim 3, wherein the control signals comprise at least one of a signal regarding starting of photographing by the at least one camera, a signal regarding a setting of a region of interest (ROI) of the at least one camera, a signal regarding an image pixel setting of the at least one camera, a signal regarding a frame rate setting of the at least one camera, a signal regarding a gain setting of the at least one camera, a signal regarding an exposure time setting of the at least one camera, a signal regarding an output intensity of light output from a projector, a signal regarding an output timing of the light output from the projector, a signal regarding communication connection of the scanner, a signal for requesting transmission of the at least one intraoral image, a signal regarding a mode setting of the scanner, and a signal regarding termination of photographing by the intraoral scanner.

12. The intraoral scanner of claim 3, further comprising a user interface configured to receive a user input, wherein the control signals comprise a signal including a request or a command corresponding to the user input.

13. The intraoral scanner of claim 3, wherein each of the at least one camera is further configured to obtain an image having a first resolution, the processor is further configured to execute the at least one instruction to obtain the image data obtained by formatting the at least one intraoral image into a frame image corresponding to a high-definition multimedia interface (HDMI) format, and the frame image is a frame image having a second resolution that is higher than the first resolution.

14. The intraoral scanner of claim 3, wherein the at least one camera is further configured to perform image capture at a first frames per second (FPS), the image data is a frame image corresponding to a second FPS that is less than the first FPS, and the processor is further configured to execute the at least one instruction to control the second communication module to transmit the frame image to the external electronic device.

* * * * *